(12) United States Patent
Mrksich et al.

(10) Patent No.: US 6,764,768 B2
(45) Date of Patent: Jul. 20, 2004

(54) CONTROLLED RELEASE COMPOSITION

(75) Inventors: Milan Mrksich, Chicago, IL (US); Christian Hodneland, Brookline, MA (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/797,166

(22) Filed: Feb. 28, 2001

(65) Prior Publication Data

US 2002/0119305 A1 Aug. 29, 2002

(51) Int. Cl.$^7$ .............................................. B32B 15/04
(52) U.S. Cl. ....................... 428/457; 428/458; 428/459; 427/299; 427/388.1; 435/6; 536/92
(58) Field of Search ................................ 478/457, 458, 478/459; 536/92; 435/6; 427/299, 388.1

(56) References Cited

U.S. PATENT DOCUMENTS

| | | | | |
|---|---|---|---|---|
| 6,159,695 A | * | 12/2000 | McGovern et al. | ............ 435/6 |
| 6,169,194 B1 | * | 1/2001 | Thompson et al. | ......... 556/429 |
| 6,284,197 B1 | * | 9/2001 | Abbott et al. | ............ 422/82.05 |
| 6,322,979 B1 | * | 11/2001 | Bamdad et al. | ................ 435/6 |
| 6,472,148 B1 | * | 10/2002 | Bamdad et al. | ................ 435/6 |
| 6,485,984 B1 | * | 11/2002 | Kim | ........................... 436/525 |
| 6,518,168 B1 | * | 2/2003 | Clem et al. | .................. 438/623 |

OTHER PUBLICATIONS

Hodneland et al. J. Am. Chem. Soc. 2000, 122, 17, 4235–4236, Apr. 14, 2000.*
Lou et al J. Am. Chem. Soc., 1983, 105, 5271–5277, Jan. 24, 1983.*
Milstien, S.; Cohen, L. A. J. Am. Chem. Soc. 1972, 94, 9158–9165.
Lau, A. N. K.; Miller, L. L. J. Am. Chem. Soc. 1983, 105, 5271–5277.
Chapter 14 of Organic Chemistry 4th ed., Morrison and Boyd, Allyn and Bacon, Inc., 1983.
E. Ruoslahti, Annu. Rev. Biochem. 1988, 57, 375–413.
Carpino, L. A.; Triolo, S. A.; Berglund, R. A. J. Org. Chem. 1989, 54, 3303–3310.
Spinke, J.; Liley, M.; Guder, H. J.; Angermaier, L.; Knoll, W. Langmuir 1993, 9, 1821–1825.
Wang, B.; Liu, S.; Borchardt, R.T. J. Org. Chem. 1995, 60, 539–543.
T. Okano, N. Yamata, J. Sakai, Y. Sakurai, Biomaterials 1995, 16, 297–303.
Mrksich, M.; Whitesides, G. M., TIBTECH. 1995, 13, 228–235.
Mrksich, M.; Grunwell, J. R.; Whitesides, G. M. J. Am. Chem. Soc. 1995, 117, 12009–12010.
Sigal, G. B.; Bamdad, C.; Barberis, A.; Strominger, J.; Whitesides, G. M. Anal. Chem. 1996, 68, 490–497.
Y. Ito, G. Chen, Y. Guan, Y. Imanishi, Langmuir 1997, 13, 2756–2759.
Mrksich, M.; Whitesides, G. M. American Chemical Society Symposium Series on Chemistry and Biological Applications of Polyethylene Glycol 1997, 680, 361–373.
C. Chothia, E. T. Jones, Annu. Rev. Biochem. 1997, 66, 823–862.
Chen, C. S.; Mrksich, M.; Huang, S.; Whitesides, G. M.; Ingber, D. E., Science 1997, 276, 1425–1428.

(List continued on next page.)

Primary Examiner—Leszek Kiliman
(74) Attorney, Agent, or Firm—Brinks Hofer Gilson & Lione

(57) ABSTRACT

An alkanethiol of formula (1):

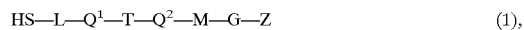

$$HS—L—Q^1—T—Q^2—M—G—Z \qquad (1),$$

may for a SAM. Under application of a potential to the surface, the leaving group —Z is released.

50 Claims, 5 Drawing Sheets

OTHER PUBLICATIONS

Mrksich, M.; Dike, L. E.; Tien, J.; Ingber, D. E.; Whitesides, G. M., *Experimental Cell Research* 1997 *235*, 305–313.

M. K. Magnusson, D. F. Mosher, *Arterioscler. Thromb. Vasc. Biol.* 1998, *18*, 1363–1370.

Roberts, C.; Chen, C. S.; Mrksich, M.; Martichonok, V.; Ingber, D. E.; Whitesides, G. M. *J. Am. Chem. Soc.* 1998, *120*, 6548–6555.

B.T. Houseman, M. Mrksich, *J. Org. Chem.* 1998, *63*, 7552–7555.

Bamdad, C. *Biophys. J.* 1998, *75*, 1997–2003.

Ding, Z.; Long, C. J.; Hayashi, Y.; Bulmus, E. V.; Joffman, A. S.; Stayton, P. S. *Bioconjugate Chem.* 1999, *10*, 395–400.

Yousaf, M. N.; Mrksich, M. *J. Am. Chem. Soc.* 1999, *121*, 4286–4287.

Zheng, A.; Shan, D.; Wang, B. *J. Org. Chem.* 1999, *64*, 156–161.

Houseman, B.T.; Mrksich, M. *Angew. Chem. Int. Ed.* 1999, *38*, 782–785.

Hodneland, C.D.; Mrksich, M. *J. Am. Chem. Soc.* 2000, *122*, 17, 4235–4236.

Chen, C.S. et al. *Biotechnol. Prog.* 1998, *14*, 353–363.

\* cited by examiner

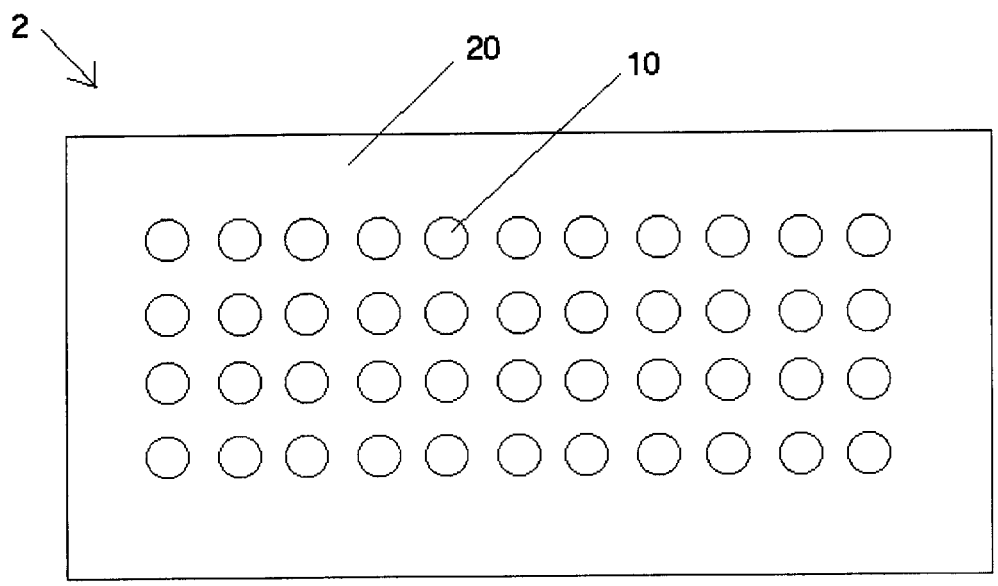
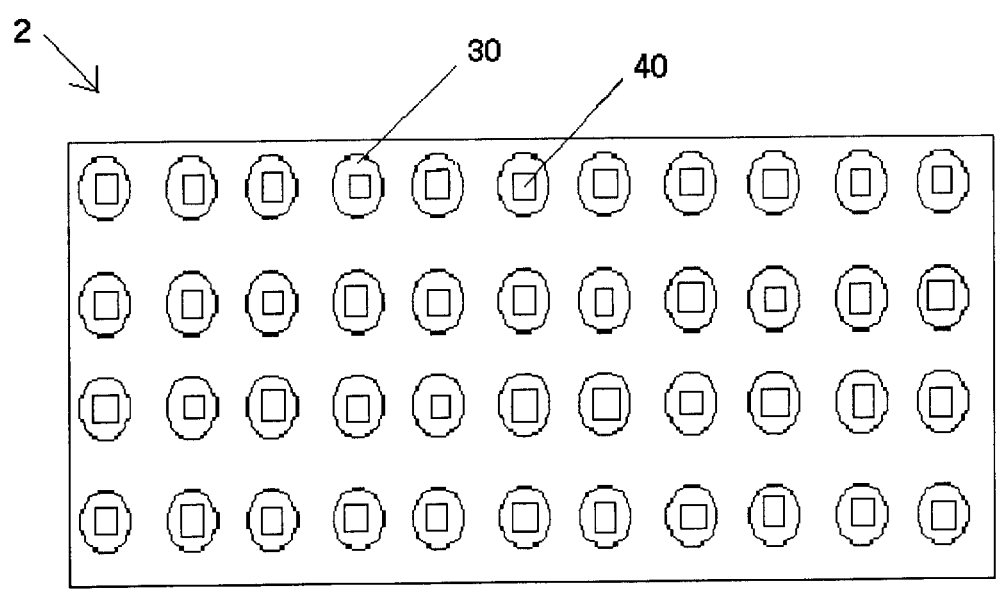

CONTROLLED RELEASE COMPOSITION

FEDERALLY SPONSORED RESEARCH OR DEVELOPMENT

The subject matter of this application was in part funded by the NSF (Grant nos. BES-9980850 and DMR-9808595). The government may have certain rights in this invention.

BACKGROUND

The present invention relates to self-assembled monolayers (SAMs) of alkanethiolates.

SAMs of alkanethiolates on gold are an important class of model substrates for mechanistic studies of the interactions of proteins and cells with surfaces. They have been used in monolayers that are inert in biological fluids—in that they prevent protein adsorption and cell adhesion—and provide surfaces for patterning the positions and shapes of attached cells (Mrksich, M.; Dike, L. E.; Tien, J. Y.; Ingber, D. E.; Whitesides, G. M. *Exp. Cell Res.* 1997, 235, 305–313; and Chen, C. S.; Mrksich, M.; Huang, S.; Whitesides, G. M.; Ingber, D. E. *Science* 1997, 276, 1345–1347). The attachment of ligands to these inert SAMs gives surfaces to which proteins and other receptors selectively bind. Monolayers presenting peptide ligands, for example, have been used to control the adhesion of cells (Roberts, C.; Chen, C. S.; Mrksich, M.; Martichonok, V.; Ingber, D. E.; Whitesides, G. M. *J. Am. Chem. Soc.* 1998, 120, 6548–6555; and Houseman, B. T.; Mrksich, M. *J. Org. Chem.* 1998, 120, 6548–6555) and monolayers presenting oligonucleotides have been used for probing gene expression in cells (Bamdad, C. *Biophys. J.* 1998, 75, 1997–2003).

A new challenge in biointerfacial science is to design dynamic substrates that can alter, in real-time, the display of ligands, and hence interactions of proteins and cells with the substrate (Lau, A. N. K.; Miller, L. L. *J. Am. Chem. Soc.* 1983, 105, 5271–5277; and Ding, Z.; Long, C. J.; Hayashi, Y.; Bulmus, E. V.; Joffman, A. S.; Stayton, P. S. *Bioconjugate Chem.* 1999, 10, 395–400). Previously, a dynamic SAM that could be switched from a state that is initially inert to a state that permits the Diels-Alder mediated immobilization of ligands has been demonstrated, which in turn provides a strategy to activate the selective binding of proteins to a substrate (Yousaf, M. N.; Mrksich, M. *J. Am. Chem. Soc.* 1999, 121, 4286–4287). Previous examples of substrates that can release attached cells have relied on a thermally responsive poly(N-isopropylacrylamide) film (T. Okano, N. Yamata, J. Sakai, Y. Sakurai, *Biomaterials* 1995, 16, 297–303; and Y. Ito, G. Chen, Y. Guan, Y. Imanishi, *Lanmuir* 1997, 13, 2756–2759).

It would be desirable to have a dynamic monolayer that can selectively release immobilized ligands. Such a monolayer could be used to regulate, in real-time, the ligand-receptor interactions between a cell and the substrate to which it is attached, and give dynamic control of the proteins presented on the surface of a monolayer. It may also be used in microsystems to regulate the release of reagents or biomolecules from a solid or gel phase.

BRIEF SUMMARY

In a first aspect, the present invention is an alkanethiol of formula (1):

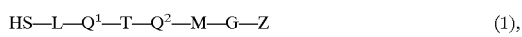

$$HS-L-Q^1-T-Q^2-M-G-Z \quad (1),$$

wherein —L— is $-(A^L_j-B^L_k-E^L_l-D^L)_m-$;

each $A^L$, $B^L$, $E^L$ and $D^L$ are individually $C(R^L_A R^L_A{}')-$, $-C(R^L_B, R^L_B{}')-$, $-C(R^L_E R^L_E{}')-$, and $-C(R^L_D R^L_D{}')-$, respectively;

each $R^L_A$, $R^L_B$, $R^L_E$ and $R^L_D$ are individually H, or any two of $R^L_A, R^L_B, R^L_E$ and $R^L_D$ together form a bond, or $R^L_A, R^L_B, R^L_E$ and $R^L_D$ together with the atoms to which they are bonded form a six-membered aromatic ring;

each $R^L_A{}'$, $R^L_B{}'$, $R^L_E{}'$ and $R^L_D{}'$ are individually H, or any two of $R^L_A{}', R^L_B{}', R^L_E{}'$ and $R^L_D{}'$ together form a bond, or $R^L_A{}', R^L_B{}', R^L_E{}'$ and $R^L_D{}'$ together with the atoms to which they are bonded form a six-membered aromatic ring;

each j, k and l are individually either 0 or 1;

m is 1 to 5;

—$Q^1$— and —$Q^2$— are each individually selected from the group consisting of

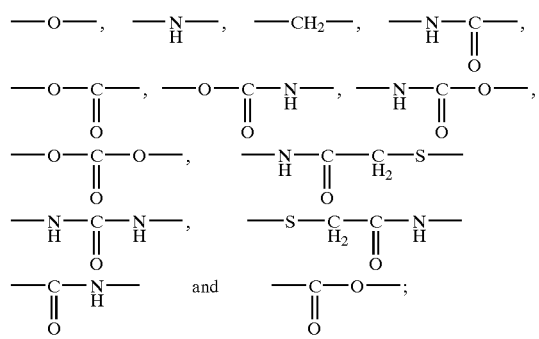

—T— is a moiety of formula (2) or formula (3)

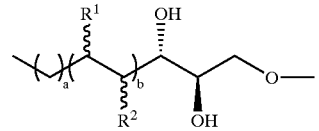

$$-(OCH_2CH_2)_nO- \quad (3)$$

$R^1$ and $R^2$ are each individually selected from the group consisting of H and OH;

a is 0 to 3;

b is 0 to 3;

∽∽∽ indicates that the chirality of the carbon atom to which it is attached may be either R or S;

n is 1 to 6;

—M— is $-(A_x-B_y-E_z-D)_w-$,

A is —O—, —S—, —N($R_A$)— or —C($R_A R_A{}'$)—;

B is —O—, —S—, —N($R_B$)— or —C($R_B R_B'$)—;

E is —O—, —S—, —N($R_E$)— or —C($R_E R_E'$)—;

D is —C($R_D R_D'$)—;

each $R_A$, $R_B$, $R_E$ and $R_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded for a ring;

each $R_A'$, $R_B'$, $R_E'$ and $R_D'$ is selected from the group consisting of H, alkyl, alkenyl, alkynyl, aryl and heterocyclic radical, or any two of $R_A'$, $R_B'$, $R_E'$ and $R_D'$ together form a bond, or any two of $R_A'$, $R_B'$, $R_E'$ and $R_D'$ together with the atoms to which they are bonded for a ring;

each x, y and z is either 0 or 1;

—G— is a moiety of formula (4)

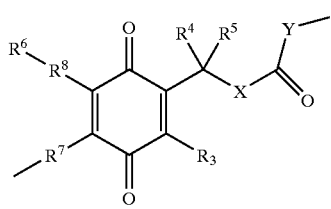

(4)

$R^3$, $R^4$, and $R^5$ are each individually a —CH$_2$— group substituted with a hydrogen or an alkyl group;

$R^6$ is a hydrogen, alkyl, alkenyl, alkynyl, aryl, halogen, heterocyclic radical or nitro group;

X is a bond or —($A^X_p$—$B^X_q$—$E^X_r$—$D^X$)$_s$—;

each $A^X$, $B^X$, $E^X$ and $D^X$ is individually C($R^X_A R^X_A'$)—, —C($R^X_B R^X_B'$)—, —C($R^X_E R^X_E'$)—, or —C($R^X_D R^X_D'$)—, respectively;

each $R^X_A$, $R^X_B$, $R^X_E$ and $R^X_D$ is individually H, or any two of $R^X_A$, $R^X_B$, $R^X_E$ and $R^X_D$ together form a bond, or $R^X_A$, $R^X_B$, $R^X_E$ and $R^X_D$ together with the atoms to which they are bonded form a six-membered aromatic ring;

each $R^X_A{'}$, $R^X_B{'}$, $R^X_E{'}$ and $R^X_D{'}$ is individually H, or any two of $R^X_A{'}$, $R^X_B{'}$, $R^X_E{'}$ and $R^X_D{'}$ together form a bond, or $R^X_A{'}$, $R^X_B{'}$, $R^X_E{'}$ and $R_{XD}{'}$ together with the atoms to which they are bonded form a six-membered aromatic ring;

each p, q and r is individually either 0 or 1;

s is 1 to 5;

Y is —O— or —NH—;

$R^7$ and $R^8$ are both single bonds, or together with the atoms to which they are bonded from one or more fused rings, substituted or unsubstituted, optionally containing heteroatoms; and —Z is a leaving group.

In a second aspect, the present invention is a disulfide of formula (5):

$$J—S—S—L—Q^1—T—Q^2—M—G—Z \quad (5),$$

where —L—, —Q$^1$—, —Q$^2$—, —T—, —M—, —G—, and —Z have the same meaning as in formula (1), —J is selected from the group consisting of H, halogen, R, —OR, —NRR', —C(O)R, and —C(O)OR;

R is selected from the group consisting of alkyl, alkenyl, alkynyl, aryl and heterocyclic radical; and R' is selected from the group consisting of H, alkyl, alkenyl, alkynyl, aryl and heterocyclic radical.

In a third aspect, the present invention is a substrate, comprising:

(i) a surface layer comprising gold, and (ii) a plurality of moieties, on at least a portion of said surface layer, wherein said moieties are alkanethiolate moieties of formula (8):

$$\text{Surf—S—L—Q}^1\text{—T—Q}^2\text{—M—G—Z} \quad (8)$$

where —L—, —Q$^1$—, —Q$^2$—, —T—, —M—, —G—, and —Z have the same meaning as in formula (1), and Surf designates where the moiety is attached to the surface.

In a fourth aspect, the present invention is a method of releasing a leaving group, comprising:

applying a reducing potential to a surface.

Definitions

"Alkyl" (or alkyl- or alk-) refers to a substituted or unsubstituted, straight, branched or cyclic hydrocarbon chain, preferably containing from 1 to 20 carbon atoms. More preferred alkyl groups are alkyl groups containing from 7 to 16 carbon atoms. Preferred cycloalkyls have from 3 to 10, preferably 3–6, carbon atoms in their ring structure. Suitable examples of unsubstituted alkyl groups include methyl, ethyl, propyl, isopropyl, cyclopropyl, butyl, isobutyl, tert-butyl, sec-butyl, cyclobutyl, pentyl, cyclopentyl, hexyl, cyclohexyl, and the like. "Alkylaryl" and "alkylheterocyclic" groups are alkyl groups covalently bonded to an aryl or heterocyclic group, respectively.

"Alkenyl" refers to a substituted or unsubstituted, straight, branched or cyclic, unsaturated hydrocarbon chain that contains at least one double bond, and preferably 2 to 20, more preferably 7 to 16, carbon atoms. Exemplary unsubstituted alkenyl groups include ethenyl (or vinyl)(—CH=CH$_2$), 1-propenyl, 2-propenyl (or allyl)(—CH$_2$—CH=CH$_2$), 1,3-butadienyl (—CH=CHCH=CH$_2$), 1-butenyl (—CH=CHCH$_2$CH$_3$), hexenyl, pentenyl, 1,3,5-hexatrienyl, and the like. Preferred cycloalkenyl groups contain five to eight carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, cyclooctatrienyl and the like.

"Alkynyl" refers to a substituted or unsubstituted, straight, branched or cyclic unsaturated hydrocarbon chain containing at least one triple bond, and preferably 2 to 20, more preferably 7 to 16, carbon atoms.

"Aryl" refers to any monovalent aromatic carbocyclic or heteroaromatic group, preferably of 3 to 10 carbon atoms. The aryl group can be monocyclic (i.e. phenyl (or Ph)) or polycyclic (i.e. naphthyl) and can be unsubstituted or substituted. Preferred aryl groups include phenyl, naphthyl, furyl, thienyl, pyridyl, indolyl, quinolinyl or isoquinolinyl.

"Halogen" (or halo-) refers to fluorine, chlorine, iodine or bromine. The preferred halogen is fluorine or chlorine.

"Heterocyclic radical" refers to a stable, saturated, partially unsaturated, or aromatic ring, preferably containing 5 to 10, more preferably 5 or 6, atoms. The ring can be substituted 1 or more times (preferably 1, 2, 3, 4 or 5 times) with a substituent. The ring can be mono-, bi- or polycyclic. The heterocyclic group consists of carbon atoms and from 1 to 3 heteroatoms independently selected from the group consisting of nitrogen, oxygen, and sulfur. The heteroatoms can be protected or unprotected. Examples of useful heterocyclic groups include substituted or unsubstituted, protected or unprotected acridine, benzathiazoline, benzimidazole, benzofuran, benzothiophene, benzothiazole, benzothiophenyl, carbazole, cinnoline, furan, imidazole, 1H-indazole, indole, isoindole, isoquinoline, isothiazole, morpholine, oxazole (i.e. 1,2,3-oxadiazole), phenazine, phenothiazine, phenoxazine, phthalazine, piperazine, pyridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i.e. 1,2,3-triazole), and the like.

"Substituted" means that the moiety contains at least one, preferably 1–3 substituent(s). Suitable substituents include hydrogen (H) and hydroxyl (—OH), amino (—NH$_2$), oxy (—O—), carbonyl (—CO—), thiol, alkyl, alkenyl, alkynyl, alkoxy, halo, nitrile, nitro, aryl and heterocyclic groups. These substituents can optionally be further substituted with 1–3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclic, and the like.

"Disulfide" means a compound containing a bond between two sulfur atoms.

"Alkanethiol" means a compound containing an alkyl group bonded to an SH group.

"Alkanethiolate" means a moiety corresponding to an alkanethiol without the hydrogen of the SH group.

"Alkylene" refers to a substituted or unsubstituted, straight, branched or cyclic hydrocarbon chain, preferably containing from 1 to 20 carbon atoms. More preferred alkylene groups are lower alkylene groups, i.e., alkylene groups containing from 1 to 6 carbon atoms. Preferred cycloalkylenes have from 3 to 10, preferably 3–6, carbon atoms in their ring structure. Suitable examples of unsubstituted alkylene groups include methylene, —(CH$_2$)$_n$—, —CH$_2$—CH(CH$_3$)—, —(C$_6$H$_{10}$)— where the carbon atoms form a six-membered ring, and the like.

"Polypeptide" refers to a molecule or moiety containing two or more amino acids bound through a peptide linkage. Examples include proteins such as antibodies, enzymes, lectins and receptors. Preferred proteins include avidin and streptavidin.

"Polynucleotide" refers to a molecule or moiety containing two or more nucleic acid such as single or double stranded RND, DNA and PNA (protein nucleic acid).

"Carbohydrate" refers to a molecule or moiety that contains one or more sugars, such as mannose, sucrose, glucose, cellulose, chitin, and chitosan.

"Ligand" refers to a binding partner of a receptor. Examples include cytokines, and chemokines.

"Hapten" refers to a molecule or moiety that will bind to an antibody specific for that hapten. Examples include fluorescein, and phosphotyrosine.

All other acronyms and abbreviations have the corresponding meaning as published in journals relative to the art of chemistry.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIG. 3 illustrates a patterned substrate.

FIG. 4 illustrates another patterned substrate.

DETAILED DESCRIPTION

Figure 1:
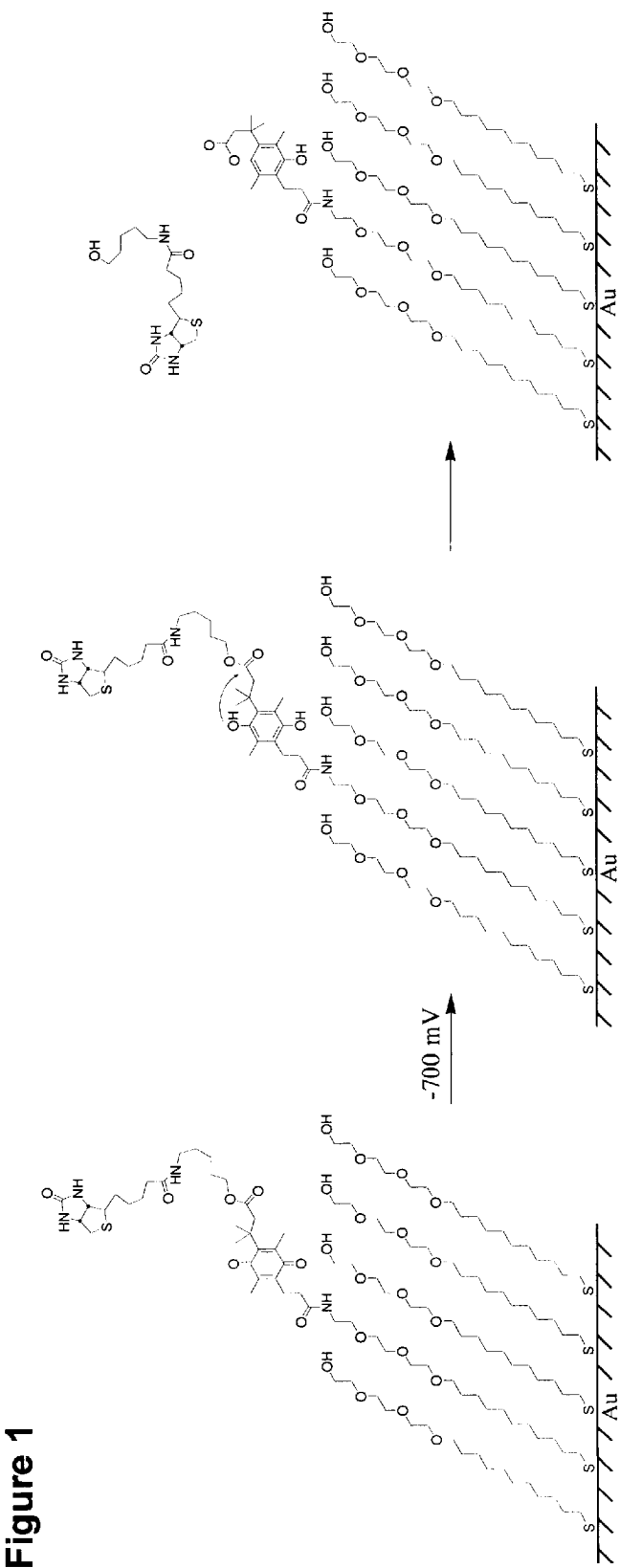
FIG. 1 is a diagram of an example of a monolayer designed to release a biotin ligand when a reductive potenial is applied to the underlying gold.

The present invention includes new alkanethiols and disulfides, and SAMs prepared from these compounds that are controlled release surfaces. The SAMs can release an attached leaving group, thereby releasing anything attached to the leaving group, such as ligands, molecules, proteins or cells, demonstrating their usefulness in biochips (such as protein chips and cell chips) and Microsystems. Reduction, either electrical or chemical, may be used as the trigger to release the leaving group. Since these films are electrically active, they also offer the advantage of efficient integration with microelectrical systems, including the use of microelectrode arrays and patterned monolayers to build surfaces that combine multiple functions.

The alkanethiols have the structure shown in formula (1):

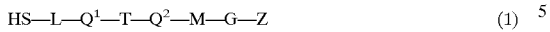

where —L— is —$(A^L_j-B^L_k-E^L_l-D^L)_m$—; each $A^L$, $B^L$, $E^L$ and $D^L$ are individually $C(R^L_A R^L_A{}')$—, —$C(R^L_B R^L_B{}')$—, —$C(R^L_E R^L_E{}')$—, and —$C(R^L_D R^L_D{}')$—, respectively; each $R^L_A$, $R^L_B$, $R^L_E$ and $R^L_D$ are individually H, or any two of $R^L_A$, $R^L_B$, $R^L_E$ and $R^L_D$ together form a bond, or $R^L_A$, $R^L_B$, $R^L_E$ and $R^L_D$ together with the atoms to which they are bonded form a six-membered aromatic ring; each $R^L_A{}'$, $R^L_B{}'$, $R^L_E{}'$ and $R^L_D{}'$ are individually H, or any two of $R^L_A{}'$, $R^L_B{}'$, $R^L_E{}'$ and $R^L_D{}'$ together with the atoms to which they are bonded form a six-membered aromatic ring; each j, k and l are individually either 0 or 1; and m is 1 to 5;

—$Q^1$— and —$Q^2$— are each individually selected from the group consisting of

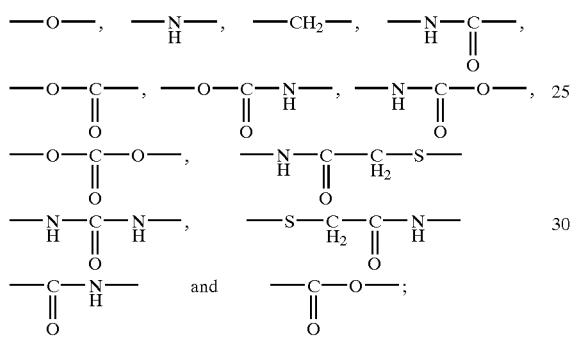

—T— is a moiety of formula (2) or formula (3)

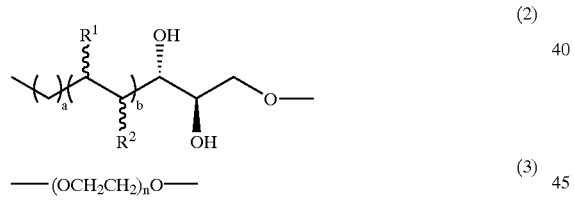

where $R^1$ and $R^2$ are each individually selected from the group consisting of H and OH; a is 0 to 3; b is 0 to 3; ∿∿ indicates that the chirality of the carbon atom to which it is attached may be either R or S; and n is 1 to 6;

—M— is —$(A_x-B_y-E_z-D)_w$—; A is —O—, —S—, —N($R_A$)— and —C($R_A R_A{}'$)—; B is —O—, —S—, —N($R_B$)— and —C($R_B R_B{}'$)—; E is —O—, —S—, —N($R_E$)— and —C($R_E R_E{}'$)—; and D is —C($R_D R_D{}'$)—; each $R_A$, $R_B$, $R_E$ and $R_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded for a ring; each $R_A{}'$, $R_B{}'$, $R_E{}'$ and $R_D{}'$ is selected from the group consisting of H, alkyl, alkenyl, alkynyl, aryl and heterocyclic radical, or any two of $R_A{}'$, $R_B{}'$, $R_E{}'$ and $R_D{}'$ together form a bond, or any two of $R_A{}'$, $R_B{}'$, $R_E{}'$ and $R_D{}'$ together with the atoms to which they are bonded for a ring; and each x, y and z is either 0 or 1;

—G— is a moiety of formula (4)

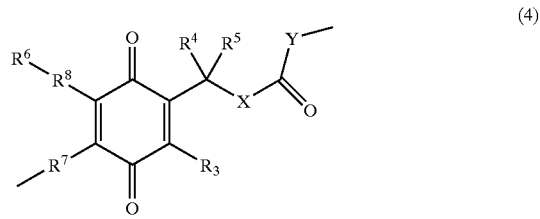

where $R^3$, $R^4$, and $R^5$ are each individually a —$CH_2$— group substituted with a hydrogen or an alkyl group; $R^6$ is a hydrogen, alkyl, alkenyl, alkynyl, aryl, halogen, heterocyclic radical or nitro group; X is a bond or —$(A^X_p-B^X_q-E^X_r-D^X)_s$—; each $A^X$, $B^X$, $E^X$ and $D^X$ are individually $C(R^X_A R^X_A{}')$—, —$C(R^X_B R^X_B{}')$—, —$C(R^X_E R^X_E{}')$—, and —$C(R^X_D R^X_D{}')$—, respectively; each $R^X_A$, $R^X_B$, $R^X_E$ and $R^X_D$ are individually H, or any two of $R^X_A$, $R^X_B$, $R^X_E$ and $R^X_D$ together form a bond, or $R^X_A$, $R^X_B$, $R^X_E$ and $R^X_D$ together with the atoms to which they are bonded form a six-membered aromatic ring; each $R^X_A{}'$, $R^X_B{}'$, $R^X_E{}'$ and $R^X_D{}'$ are individually H, or any two of $R^X_A{}'$, $R^X_B{}'$, $R^X_E{}'$ and $R^X_D{}'$ together form a bond, or $R^X_A{}'$, $R^X_B{}'$, $R^X_E{}'$ and $R^X_D{}'$ together with the atoms to which they are bonded form a six-membered aromatic ring; each p, q and r are individually either 0 or 1; and s is 1 to 5; Y is —O— or —NH—; and $R^7$ and $R^8$ are both single bonds, or together with the atoms to which they are bonded from one or more fused rings, substituted or unsubstituted, optionally containing heteroatoms; and —Z is a leaving group.

The disulfides have the structure shown in formula (5):

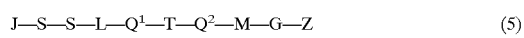

where —L—, —$Q^1$—, —$Q^2$—, —T—, —M—, —G—, and —Z have the same meaning as in formula (1), and —J is selected from the group consisting of H, halogen, R, —OR, —NRR', —C(O)R, and —C(O)OR; R is selected from the group consisting of alkyl, alkenyl, alkynyl, aryl and heterocyclic radical; R' is selected from the group consisting of H, alkyl, alkenyl, alkynyl, aryl and heterocyclic radical.

Preferably, —L— contains 6 to 20 carbon atoms, more preferably 8 to 18 carbon atoms. Preferably, —L— contains 1 or 0 double bonds, or 1 triple bond. Most preferably, —L— is an alkylene containing 6 to 18 carbon atoms.

Preferably, —$Q^1$— is —O— or —$CH_2$—.

Preferably, —$Q^2$— is selected from the group consisting of

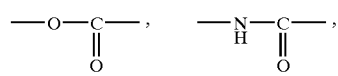

-continued

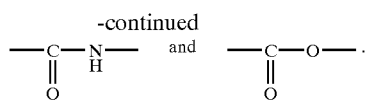

Preferably, —T— is a moiety of formula (3)

$$-(OCH_2CH_2)_nO- \quad (3),$$

most preferably n is 3.
Preferably, —J is a moiety of formula (6)

$$-(CH_2)_t(OCH_2CH_2)_uOH \quad (6),$$

where t is 2 to 20, and u is 2 to 10; more preferably u is 3 to 6.

Preferably —M— is an alkylene group containing 1 to 10 carbon atoms.

Preferably —G— is a moiety of formula (4')

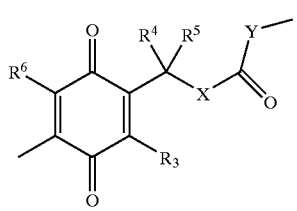
(4')

Preferably, $R^3$, $R^4$, and $R^5$ are each individually a —$CH_3$ or —$CH_2CH_3$; preferably $R^6$ is an alkyl, more preferably a —$CH_3$ or —$CH_2CH_3$. Preferably X is bond or an alkylene group containing 1–3 carbon atoms, more preferably a —$CH_2$— group.

Z may be any group, and preferably —Z contains a polypeptide, a polynucleotide, a carbohydrate, a lectin, a ligand (such as biotin), a diene, a dienophile, or a hapten; more preferably —Z also contains a group of formula (7)

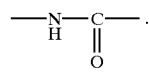
(7)

Aromatic ring systems are well known to those of ordinary skill in the art, and are described in chapter 14 of "Organic Chemistry" 4th ed., Morrison and Boyd (Allyn and Bacon, Inc., 1983). Examples of one or more fused rings include aromatic rings such as benzene, naphthalene and anthracene, as well as aliphatic rings such as cyclohexene and cyclopentene.

The alkanethiols and disulfides of the present invention may be synthesized using reagents and reaction well known to those of ordinary skill in the art, such as those described in "Advanced Organic Chemistry" J. March (Wiley & Sons, 1994); and "Organic Chemistry" 4th ed., Morrison and Boyd (Allyn and Bacon, Inc., 1983).

For example, in the case where —$Q^2$— is an amide linkage, and —Z contains an amide linkage (formula (7)), a disulfide of formula (5) may be formed by reacting the compound of formula (10) with the compound of formula (11):

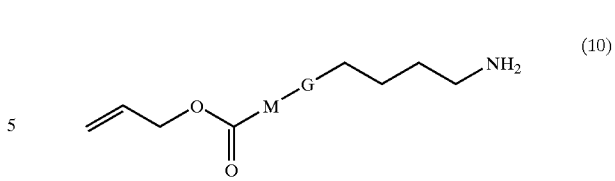
(10)

$$NHS-Z^1 \quad (11)$$

to form the compound of formula (12):

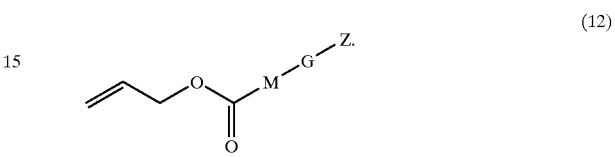
(12)

Further reaction of the compound of formula (12), with for example, $(PPh_3)_4Pd$ and morpholine, followed by reaction with DCC and NHS, will yield the compound of formula (13):

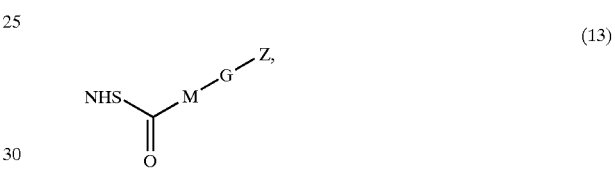
(13)

which may then be reacted with the compound of formula (14):

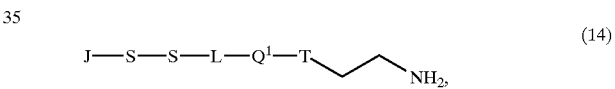
(14)

to form the disulfide. The corresponding alkanethiols may be prepared by reducing the —S—S— bond. In formula (11), —$Z^1$ is a group contained in —Z, such that —Z is

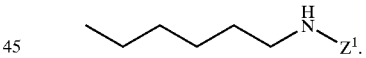

The compounds of formulas (10), (11) and (14) may be prepared by methods known to those of ordinary skill in the art; additional syntheses are provided in the examples.

When applied to a surface containing gold, the alkanethiols and disulfides will form SAMs. In the case of the alkanethiols, the hydrogen is lost, and the remaining moiety attaches to the surface through the sulfur atom. In the case of the disulfides, the disulfide bridge is broken, and the remaining moieties attach to the surface through the sulfur atoms. The surface preferably has a plurality of alkanethiolate moieties shown in formula (8)

$$Surf-S-L-Q^1-T-Q^2-M-G-Z \quad (8)$$

where —L—, $Q^1$—, $Q^2$—, —T—, —M—, —G—, and —Z have the same meaning as in formula (1), and Surf designates where the moiety attaches to the surface. The density of moieties on the surface is typically $10^{10} \pm 5\%$ per square centimeter. The moieties of the present invention may cover the entire surface alone or with other moieties, or may be patterned on the surface alone or with other moieties. Patterning may be carried out by, for example, by microprinting, as described in Mrksich, M.; Dike, L. E.; Tien, J.; Ingber, D. E.; Whitesides, G. M., *Experimental Cell Research* 1997 235, 305–313; Chen, C. S.; Mrksich, M.; Huang, S.; Whitesides, G. M.; Ingber, D. E., *Science* 1997, 276, 1425–1428; and Mrksich, M.; Whitesides, G. M., *TIBTECH*. 1995, 13, 228–235.

Preferably the surface contains gold, more preferably the surface contains 50 to 100 atom percent gold. Preferably, the surface is pure or fine gold, or an alloy of gold with copper, silver, or a combination thereof.

The surface may be on a base. The base may have the same composition as the surface (for example a gold surface on a gold plate), or the surface may be, for example, a film, foil, sheet, or plate, on a base having a different composition. The base may be any material, such as metal, ceramic, plastic, or a natural material such as wood. Examples of bases include glass, quartz, silicon, transparent plastic, aluminum, carbon, polyethylene and polypropylene.

The surface material may be attached to the base by any of a variety of methods. For example, a film of the surface material may be applied to the base by sputtering or evaporation. If the surface material is a foil or sheet, in could be attached with an adhesive. Furthermore, the surface need not completely cover the base, but may cover only a portion of the base, or may form a pattern on the base. For example, sputtering the base, covering those portions of the base where no surface material is desired, may be used to pattern portions of the base. These patterns may include an array of regions containing, or missing, the surface material.

The —G— moiety is easily reduced, converting the ring system in this moiety to an aromatic ring system, and replacing the carbonyl oxygens with hydroxyl groups. Since the ring system becomes aromatic, the carbonyl oxygens are easily reduced. The reduction may be done electrochemically, or chemically. Once formed, one of the hydroxyl groups will react with the ester or amide moiety of the —G— moiety:

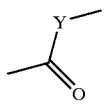

resulting in cyclic esterification to form a lactone, and releasing an H$_2$N—Z or HO—Z molecule. Similar chemistry, using for example quinone propionic esters and amides, has been used as protecting groups for alcohols and amines, respectively, because mild chemical reduction causes rapid lactonization with liberation of an alcohol or amine (Carpino, L. A.; Triolo, S. A.; Berglund, R. A. *J. Org. Chem.* 1989, 54, 3303–3310; Wang, B.; Liu, S.; Borchardt, R. T. *J. Org. Chem.* 1995, 60, 539–543; Zheng, A.; Shan, D.; Wang, B. *J. Org. Chem.* 1999, 64, 156–161; and Milstien, S.; Cohen, L. A. *J. Am. Chem. Soc.* 1972, 94, 9158–9165).

A reducing potential may be applied to the surface on which SAMs of the present invention are formed, electricly. Preferably, the potential has a magnitude of at most –2 V, more preferably at most –1.2 V, even more preferably at most –900 mV, and most preferably at most –700 mV. All potentials are relative an Ag/AgCl/KCl reference electrode.

A cell chip is an array of regions containing cells on a surface, separated by regions containing no cells or cells at a much lower density. A cell chip may be prepared by applying SAMs of the present invention (or SAMs containing a mixture of the moiety of formula (8) and moiety that produce an inert surface, such as moieties terminated in short oligomers of the ethylene glycol group: (OCH$_2$CH$_2$)$_n$OH, n=3–6) on regions of the surface that are to have cells attached (or is intended to have cells at a higher density). The remaining regions could be left uncovered, or could be cover with SAMs that are inert.

For example, FIG. 3 illustrates one possible pattern, where circles 10 contain a SAM of the present invention, and the remainder 20 of the surface is covered with a SAM that presents an inert surface, all on a surface 2. Another example, FIG. 4 illustrates another possible pattern, where squares 40 contain a SAM of the present invention, and regions 30 surrounding the squares contain a SAM that presents an inert surface, all on a surface 2.

Once the surface is patterned as desired, the cells may be allowed to attach and proliferate in the regions containing SAMs of the present invention, by contacting those regions with cells, and providing the nutrients and conditions necessary for the cells to proliferate.

A protein chip is an array of regions containing protein, separated by regions containing no protein or protein at a much lower density. In the same manner as a cell chip may be prepared, a protein chip may be prepared by applying SAMs of the present invention on regions of the surface that are to remain have protein (or intended to have protein at a higher density). The remaining regions could be left uncovered, or could be cover with SAMs that present an inert surface. The same variety of patterns is possible with protein chips as described above for cell chips; FIGS. 3 and 4 are two possible patterns. The protein chip may then be prepared by contacting the surface with the desired protein or proteins.

EXAMPLES

Example 1

The compound of formula (15) was prepared as outlined in the following synthesis scheme. In the scheme, abbreviations have the following meanings: MOMCl is chloromethyl methyl ether; DIPEA is diisopropylethyl amine; PCC is pyridinium chlorochromate; MOM is methylmethoxy; DCC is dicyclohexylcarbodiimide; DMAP is 4-dimethylaminopyridine; TMSBr is trimethylsilylbromide; NBS is N-bromosuccinimide; Fmoc is fluoronylmethoxycarbonyl; —NHS is an N-hydroxysuccinimide ester of the group to which it is attached; NHS is N-hydroxysuccinimide; Boc is t-butyloxycarbonyl; and AIBN is 2,2'-azobisisobutyronitrile. Furthermore, in the synthetic scheme, the use of NHS may be replaced with HOBt (N-hydroxybenzotriazole) to form the corresponding product.

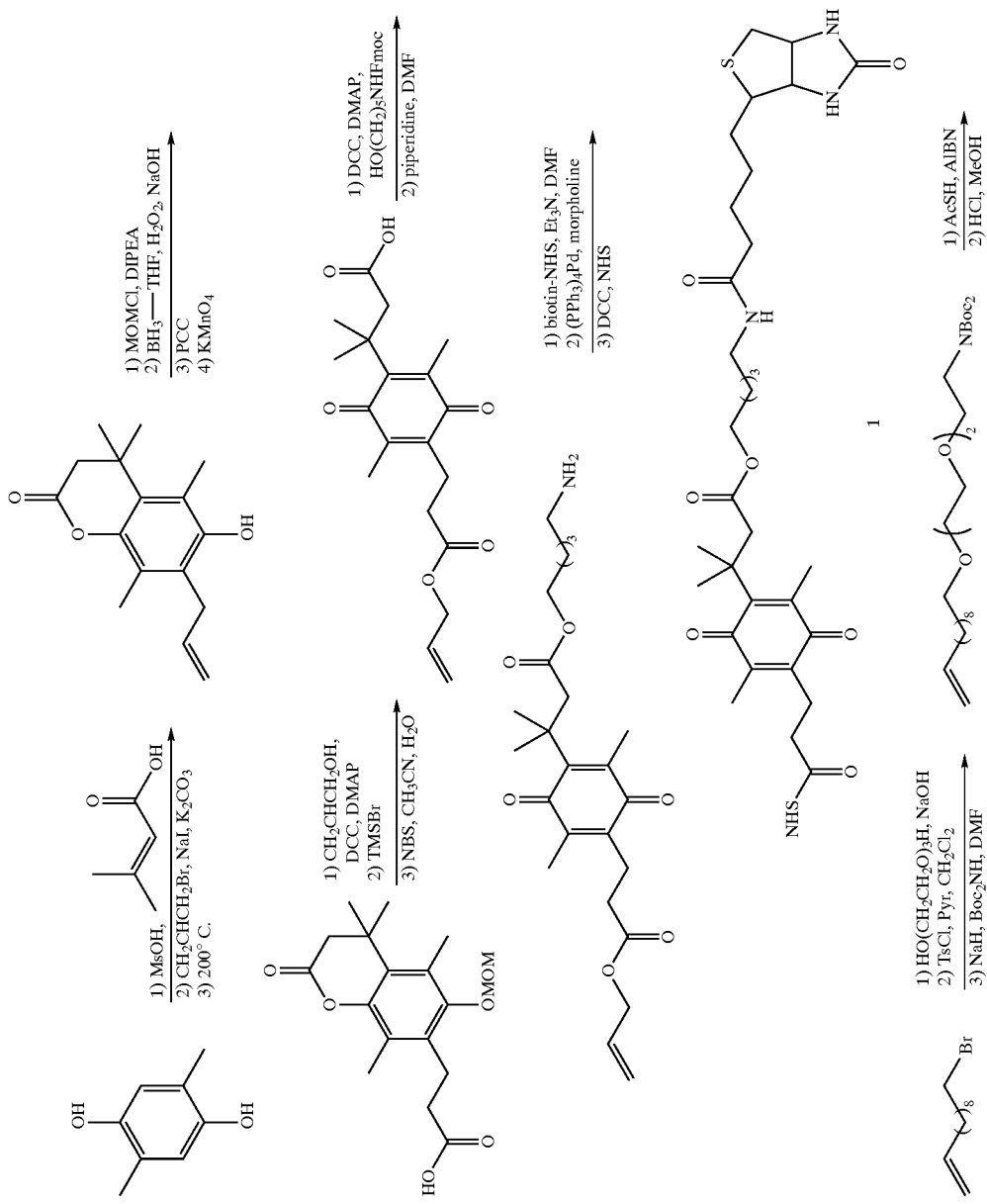

-continued
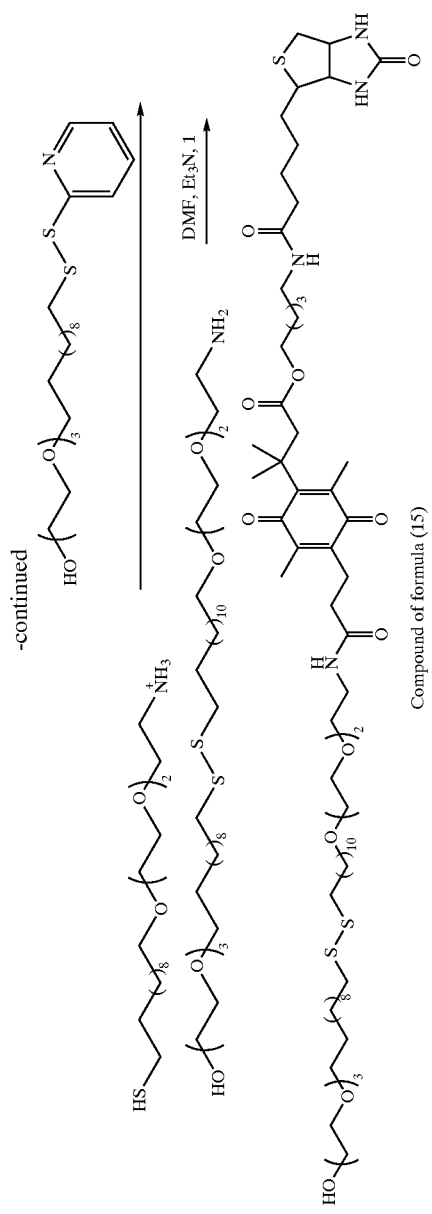
Compound of formula (15)

6-Hydroxy-4,4,5,8-tetramethyl-chroman-2-one (A). 2,5-Dimethylbenzoquinone (10 g, 73.5 mmol) was dissolved in 300 mL of ether, which was mixed with an aqueous solution of sodium hydrosulfite (178 g in 150 mL of water, 85% pure, 870 mmol). The mixture was shaken until the ether layer became nearly colorless. The ether layer was separated, and the aqueous layer was extracted with ethyl ether (3×200 mL). The combined ether layers were washed with brine (2×150 mL) and dried over $MgSO_4$. Filtration and solvent evaporation gave 10.03 g (72.6 mmol) of the hydroquinone as a white solid.

The hydroquinone was mixed with 3,3-dimethylacrylic acid (8.01 g, 80 mmol) and methanesulfonic acid (100 mL). The mixture was stirred at 85° C. under nitrogen for 3 h and then cooled to room temperature. To the mixture was added 300 g of ice with stirring. The precipitate was extracted with ethyl acetate (4×100 mL). The combined organic layers were washed with saturated $NaHCO_3$ (2×100 mL) and water (2×100 mL) and dried over $MgSO_4$. After filtration and evaporation, a residue was obtained, which was recrystallized from hexane and ethyl acetate (1:1, v/v) to give 13.02 g (81%) of the desired product. $^1$H NMR 500 MHz ($CDCl_3$) δ6.57 (s, 1H) 4.85 (s, 1H), 2.56 (s, 2H), 2.33 (s, 3H), 2.22 (s, 3H), 1.46 (s, 6H).

6-Allyloxy-4,4,5,8-tetramethyl-chroman-2-one (B). The lactone A (7.08 g, 32.17 mmol) and allyl bromide (7.79 g, 64.35 mmol) were dissolved in 50 mL of acetone. $K_2CO_3$ (8.88 g, 64.35 mmol) and NaI (0.2 g) were added into the solution. The mixture was stirred at 60° C. for 80 h and then evaporated. The residue was partitioned between water and methylene chloride. The organic layer was separated. The aqueous layer was further extracted with methylene chloride (4×50 mL), and the combined $CH_2Cl_2$ layers were washed with water (3×50 mL) and dried over $MgSO_4$. Solvent evaporation gave 8.26 g (99%) of a white solid (B). $^1$H NMR 500 MHz ($CDCl_3$) δ6.63 (s, 1H), 6.13–6.01 (m,1H), 5.46–5.26 (m, 2H), 4.50 (d, J=5.1 Hz, 2H), 2.56 (s, 2H), 2.35 (s, 3H), 2.27 (s, 3H), 1.46 (s, 6H).

7-Allyl-6-hydroxy-4,4,5,8-tetramethyl-chroman-2-one (C). Compound B (2.9 g, 11.1 mmol) was heated at 200° C. under $N_2$ for 7 h. Purification by flash chromatography ($CH_2Cl_2$) gave 2.61 g (90%) of the rearranged product C. $^1$H NMR 500 MHz ($CDCl_3$) δ5.99–5.88 (m, 1H), 5.12 (m, 2H), 4.76 (s,1H), 3.41 (dt, J=6 Hz, 1.5 Hz, 2H), 2.53 (s, 2H), 2.33 (s, 3H), 2.21 (s, 3H), 1.44 (s, 6H).

7-Allyl-6-methoxymethoxy-4,4,5,8-tetramethyl-chroman-2-one (D). Compound C (8.26 g, 31.65 mmol) and DIPEA (57.2 mL, 317.7 mmol) were dissolved in 160 mL of methylene chloride. The mixture was cooled in an ice-water bath and stirred under $N_2$. Methoxymethyl chloride (12.2 mL, 159 mmol) was added dropwise. After the addition, the mixture was stirred at room temperature under $N_2$ overnight. The mixture was diluted with 140 mL of methylene chloride and washed with 10% HCl solution (2×50 mL) and water (3×50 mL) and dried over $MgSO_4$. Filtration and solvent evaporation gave a yellow residue, which was purified on a silica gel column (hexanes and ethyl acetate, 3/1, v/v) to give 8.61 g (87%) of a solid product. $^1$H NMR ($CDCl_3$) δ5.96 (m, 1H), 5.07–4.95 (m, 2H), 4.90 (s, 2H), 3.63 (s, 3H), 3.47 (d, J=5.7 Hz, 2H), 2.58 (s, 2H), 2.40 (s, 3H), 2.22 (s, 3H), 1.47 (s, 6H).

7-(3-Hydroxy-propyl)-6-methoxymethoxy-4,4,5,8-tetramethyl-chroman-2-one (E). Compound D (4.09 g, 13.46 mmol) was dissolved in 7 mL of freshly distilled THF. Argon was passed through the mixture for 20 min. The solution was cooled in an ice-water bath. $BH_3$—THF solution (1.0 M, 5.05 mL, 5.05 mmol) was added dropwise with stirring. After the addition, the mixture was stirred at 0° C. for 2 h. Water (about 1 mL) was added dropwise to destroy the excess borane until hydrogen evolution ceased. NaOH solution (2 N, 3.4 mL) and 30% $H_2O_2$ solution (1.7 mL, 16.2 mmol) were added. The mixture was stirred for 30 min and neutralized with 5% HCl solution. The organic compounds were extracted with EtOAc (3×50 mL), washed with water (3×30 mL), and dried over $MgSO_4$. The solvent was evaporated, and the residue was purified on a silica gel column (EtOAc/hexanes=1/3, v/v) to give 3.19 g (70%) of the product. $^1$H NMR ($CDCl_3$) δ4.91 (s, 2H), 3.63 (s, 3H), 3.60 (t, J=6.0 Hz, 2H), 2.81 (t, J=7.4 Hz, 2H), 2.56 (s, 2H), 2.38 (s, 3H), 2.24 (s, 3H), 1.77 (m, 2H), 1.45 (s, 6H).

3-(6-Methoxymethoxy-4,4,5,8-tetramethyl-2-oxo-chroman-7-yl)-propionic acid (F). Compound E (2.11 g, 6.55 mmol) was dissolved in 50 mL of methylene chloride. PCC (2.127 g, 9.89 mmol) was added in portions with stirring at room temperature. The total reaction time was 3.5 h. The reaction mixture was filtered through a short silica gel column, and washed with a solution of ethyl acetate and hexanes (1:1, v/v). The filtrate was evaporated to give the aldehyde (1.97 g) which was dissolved in 8 mL of acetone and 2 mL of water, and then $KMnO_4$ (1.00 g) was added. The mixture was stirred for 1 h and then acidified with 5% HCl solution. The white precipitate was extracted with ethyl acetate (3×30 mL), washed with water (3×15 mL), and dried over $MgSO_4$. Filtration and solvent evaporation gave 1.27 g (58%) of the product. $^1$H NMR ($CD_3OD$) δ4.91 (s, 2H), 3.58 (s, 3H), 3.02 (t, J=8.6 Hz, 2H), 2.59 (s, 2H), 2.46 (t, J=8.6 Hz, 2H), 2.38 (s, 3H), 2.23 (s, 3H), 1.43 (s, 6H).

3-(6-Methoxymethoxy-4,4,5,8-tetramethyl-2-oxo-chroman-7-yl)-propionic acid allyl ester (G). To a solution of F (918 mg, 2.73 mmol) in 20 mL of ethyl acetate was added allyl alcohol (204 μL, 3.0 mmol), 4-(dimethylamino)pyridine (34 mg, 0.273 mmol), and DCC (619 mg, 3.0 mmol). The solution was stirred at room temperature for 12 h. The white precipitate that formed was filtered off and the filtrate was evaporated. The residue was purified using column chromatography with hexanes/ethyl acetate (4:1, v/v) to give 709 mg (69%) of compound G as a yellow oil. $^1$H NMR 400 MHz ($CDCl_3$) δ5.88 (m, 1H), 5.25 (m, 2H), 4.86 (s, 2H), 4.56 (dt, J=5.6 Hz, 1.2 Hz, 2H), 3.56 (s, 3H), 2.99 (t, J=8.6 Hz, 2H), 2.51 (s, 2H), 2.50 (t, J=8.6 Hz, 2H), 2.31 (s, 3H), 2.20 (s, 3H), 1.40 (s, 6H).

3-(6-Hydroxy-4,4,5,8-tetramethyl-2-oxo-chroman-7-yl)-propionic acid allyl ester (H). The compound G (393 mg, 1.04 mmol) was dissolved in 10 mL of methylene chloride and cooled to −35° C. Bromotrimethylsilane (414 μL, 3.13 mmol) was added dropwise, and the solution was stirred for 1 h. A solution of saturated $NaHCO_3$ (15 mL) was added followed by extraction with methylene chloride (2×30 mL). The organic layers were combined and dried with $MgSO_4$. After filtration and evaporation, the residue was purified using column chromatography with hexanes/ethyl acetate (4:1, v/v) to give 262 mg (76%) of the compound H as a white oily solid. $^1$H NMR 400 MHz ($CDCl_3$) δ7.80 (s, 1H), 5.87 (m, 1H), 5.25 (m, 2H), 4.58 (d, J=5.6 Hz, 2H), 2.92 (t, J=5.5 Hz, 2H), 2.72 (t, J=5.6 Hz, 2H), 2.50 (s, 2H), 2.36 (s, 3H), 2.19 (s, 3H), 1.43 (s, 6H).

3-[4-(2-Allyloxycarbonyl-ethyl)-2,5-dimethyl-3,6-dioxo-cyclohexa-1,4-dienyl]-3-methyl-butyric acid (I). To a solution of lactone H (262 mg, 0.79 mmol) in a mixture of acetonitrile (9 mL), and water (2 mL) was added NBS (147 mg, 0.83 mmol) in portions with stirring at room temperature. After stirring at room temperature for 30 min, the organic solvents were evaporated under reduced pressure, and the remaining solution was extracted with methylene chloride (2×30 mL). After drying over $MgSO_4$, the solvent was evaporated to give a yellow oily product, which was used without further purification. $^1$H NMR 400 MHz (CDCl$_3$) δ5.83 (m, 1H), 5.20 (m, 2H), 4.51 (dt, J=5.6 Hz, 1.2 Hz, 2H), 2.93 (s, 2H), 2.69 (t, J=8 Hz, 2H), 2.43 (t, J=8 Hz, 2H), 2.06 (s, 3H), 1.92 (s, 3H), 1.37 (s, 6H).

3-[4-(2-Allyloxycarbonyl-ethyl)-2,5-dimethyl-3,6-dioxo-cyclohexa-1,4-dienyl]-3-methyl-butyric acid 5-(9H-fluoren-9-ylmethoxycarbonylamino)-pentyl ester (J). 5-N-(9-fluorenylmethyloxycarbonyl)aminopentan-1-ol (257 mg, 0.79 mmol) and crude compound 1 from above were dissolved in 10 mL of methylene chloride. 4-(dimethylamino)pyridine (10 mg, 79 μmol) was added, followed by DCC (180 mg, 0.87 mmol). The solution was stirred at room temperature for 12 h. The white preciptitate that formed was filtered off and the filtrate was evaporated. The residue was purified using column chromatography with hexanes/ethyl acetate (4:1, v/v) to give 308 mg (60% over 2 steps) of compound J as a yellow oil. $^1$H NMR 400 MHz (CDCl$_3$) δ7.73 (d, J=7.6 Hz, 2H), 7.56 (d, J=7.6 Hz, 2H), 7.36 (t, J=7.6 Hz, 2H), 7.28 (t, J=7.6 Hz, 2H), 5.87 (m, 1H 5.24 (m, 2H), 4.87 (br t, J=6 Hz) 4.54 (dt, J=5.6 Hz, 1.2 Hz, 2H), 4.37 (d, J=6.8 Hz, 2H), 4.18 (t, J=6.8 Hz, 1H), 3.93 (t, J=6.4 Hz, 2H), 3.14 (q, J=6 Hz, 2H), 2.92 (s, 2H), 2.73 (t, J=8 Hz, 2H), 2.47 (t, J=8 Hz, 2H), 2.10 (s, 3H), 1.98 (s, 3H), 1.58–1.42 (br, 4H), 1.38 (s, 6H), 1.30 (m, 2H).

3-[4-(2-Allyloxycarbonyl-ethyl)-2,5-dimethyl-3,6-dioxo-cyclohexa-1,4-dienyl]-3-methyl-butyric acid 5-amino-pentyl ester (K). To a solution of the compound J (250 mg, 0.38 mmol) dissolved in 10 mL of DMF was added piperidine (0.5 mL). The solution was stirred 10 min at room temperature. The solvent was evaporated and the residue was purified by flash chromatography using a gradient solvent system 10% MeOH/CH$_2$Cl$_2$ to 100% MeOH. After evaporation of the solvent 53 mg (33%) of the compound K was isolated as a yellow oil. $^1$H NMR 500 MHz (CD$_3$OD) δ5.87 (m, 1H), 5.22 (m, 2H), 4.54 (dt, J=5.6 Hz, 1.2 Hz, 2H), 3.93 (t, J=7 Hz, 2H), 2.92 (s, 2H), 2.72 (t, J=8 Hz, 2H), 2.68 (t, J=7.5 Hz, 2H), 2.45 (t, J=8 Hz, 2H), 210 (s, 3H), 1.96 (s, 3H), 1.58–1.42 (br, 4H), 1.38 (s, 6H), 1.30 (m, 2H).

3-[4-(2-Allyloxycarbonyl-ethyl)-2,5-dimethyl-3,6-dioxo-cyclohexa-1,4-dienyl]-3-methyl-butyric acid 5-[5-(2-oxo-hexahydro-thieno[3,4-d]imidazol-6-yl)-pentanoylamino]-pentyl ester (L). To a solution of amine K (43 mg, 0.1 mmol) in 5 mL of DMF was added biotinyl-N-hydroxysuccinimide ester (39 mg, 0.13 mmol) followed by triethylamine (29 μL, 0.2 mmol). The solution was stirred at room temperature for 15 h. After evaporation of the solvent, the residue was purified by column chromatography (CH$_2$Cl$_2$/MeOH, 10:1. v/v) to give 34 mg (53%) of the compound L as a yellow solid. $^1$H NMR 500 MHz (CD$_3$OD) δ5.92 (m, 1H), 5.29 (m, 2H), 4.56 (dt, J=5.6 Hz, 1.2 Hz, 2H), 4.48 (dd, J=8 Hz, 4.5 Hz, 1H), 4.29 (dd, J=8 Hz, 4.5 Hz, 1H), 3.97 (t, J=7 Hz, 2H), 3.20 (m, 1H), 3.14 (m, 1H), 2.93 (s, 2H), 2.90 (m, 1H), 2.74 (t, J=8 Hz, 2H), 2.69 (d, J=12.5 Hz, 1H), 2.48 (t, J=8 Hz, 2H), 2.19 (t, J=7.5 Hz, 2H), 2.12 (s, 3H), 1.98 (s, 3H), 1.78–1.52 (br, 6H), 1.52–1.38 (br, 4H), 1.42 (s, 6H), 1.30 (m, 2H).

3-[4-(2-Carboxy-ethyl)-2,5-dimethyl-3,6-dioxo-cyclohexa-1,4-dienyl]-3-methyl-butyric acid 5-[5-(2-oxo-hexahydro-thieno[3,4-d]imidazol-6-yl)-pentanoylamino]-pentyl ester (M). To a solution of the compound L (34 mg, 53 μmol) in 4 mL of THF was added tetrakis(triphenylphosphine)palladium(0) (6 mg, 5.3 μmol) followed by morpholine (46 μL, 0.53 mmol). After evaporation of the solvent, the residue was purified by flash chromatography using a gradient solvent system 10% MeOH/CH$_2$Cl$_2$ to 100% MeOH to give 12 mg (40%) of the compound M as a yellow solid. $^1$H NMR 400 MHz (CDCl$_3$) δ7.05 (s, 1H), 6.10 (s, 1H), 5.16 (s, 1H), 4.51 (dd, J=8 Hz, 4.5 Hz, 1H), 4.35 (dd, J=8 Hz, 4.5 Hz, 1H), 3.93 (t, J=7 Hz, 2H), 3.72 (t, J=5.4 Hz, 1H), 3.17 (m, 2H), 2.93 (s, 2H), 2.90 (m, 1H), 2.72 (m, 2H), 2.40 (t, J=8 Hz, 2H), 2.19 (t, J=7.5 Hz, 2H), 2.12 (s, 3H), 1.98 (s, 3H), 1.78–1.52 (br, 6H), 1.52–1.38 (br, 4H), 1.42 (s, 6H), 1.30 (m, 2H).

Toluene-4-sulfonic acid 2-[2-(2-undec-10-enyloxyethoxy)-ethoxy]-ethyl ester (O). 2-[2-(2-undec-10-enyloxyethoxy)-ethoxy]-ethanol (prepared by the method described in Sigal, G. B.; Bamdad, C.; Barberis, A.; Strominger, J.; Whitesides, G. M. Anal. Chem. 1996, 68, 490–497) (3.21 g, 10.6 mmol) was dissolved in 5 mL of pyridine and cooled to 0° C. Tosyl chloride (3.03 g, 15.9 mmol) was dissolved in 20 mL of dry CH$_2$Cl$_2$ and added dropwise to the solution of 2-[2-(2-undec-10-enyloxy-ethoxy)-ethoxy]-ethanol. After stirring at 0° C. for 8 h, the solution was added to ice water and extracted with methylene chloride (3×100 mL). The combined organic layers were washed water (2×50 mL) and dried over MgSO$_4$. After filtration and evaporation, the residue was purified by column chromatography (hexanes/EtOAc, 4:1, v/v) resulting in 3.1 g (64%) of pure compound O.

DiBOC protected amine (P). To a solution of Di-tert-butyl iminodicarboxylate (1.05 g, 4.82 mmol) in 10 mL of DMF at 0° C. was added sodium hydride (60%, 193 mg, 4.82 mmol). After stirring at room temperature for 30 min, a solution of compound O (2 g, 4.38 mmol) in 10 mL of DMF was added dropwise. The solution was heated to 50° C. and stirred for 20 h. After cooling to room temperature, the solution was quenched with water (0.5 mL), and the solvent was evaporated. The residue was purified by column chromatography (hexanes/EtOAc, 4:1, v/v) to give 2.2 g (99%) of pure compound P as a colorless oil.

DiBOC thiolacetate (Q). To a solution of compound P (370 mg, 0.74 mmol) in 10 mL of THF was added thioletic acid (158 μL, 2.2 mmol) followed by AlBN (25 mg). The solution was irradiated in a photochemical reactor (Rayonet reactor lamp, Southern New England Ultraviolet Co., model no. RPR-100) for 5 h. After concentration of the reaction mixture, the residue was purified by column chromatography (hexanes/EtOAc, 4:1, v/v) to give 389 mg (91%) of pure compound Q as a colorless oil.

11-{2-[2-(2-Ammoniumchloride-ethoxy)-ethoxy]-ethoxy}-undecane-1-thiol (R). To a solution of compound Q (5.98 g, 10.3 mmol) dissolved in 150 mL of MeOH was added HCl (12N, 10 mL). After stirring for 12 h at reflux, the solution was cooled to room temperature, and the solvent was evaporated. The residue was purified by flash chromatography (CH$_2$Cl$_2$/MeOH, 5:1, v/v) to afford 3.6 g (99%) of compound R.

2-(2-{2-[11-(Pyridin-2-yldisulfanyl)-undecyloxy]-ethoxy}-ethoxy)-ethanol (S). Aldrithiol-2 (1.45 g, 6.59 mmol) was added to a solution of 2-{2-[2-(11-mercapto-undecyloxy)-ethoxy]-ethoxy}-ethanol (1.85 g, 5.49 mmol) in 30 mL of MeOH. After stirring the solution for 42 h at room temperature, the solvent was evaporated, and the residue was purified by flash chromatography (EtOAc) to afford compound S 1.97 g (81%).

Amino alcohol disulfide (T). To a solution of compound S (643 mg, 1.44 mmol) in 10 mL of MeOH was added compound R (533 mg, 1.57 mmol). The solution was stirred at room temperature for 40 h. After concentration, the reaction mixture was purified by flash chromatography (gradient: $CH_2Cl_2$/MeOH, 10:1 to 5:1, v/v) to afford 708 mg (73%) of compound T.

Biotin quinone disulfide (U). To a solution of compound M (20 mg, 33 $\mu$mol) dissolved in 3 mL of DMF was added compound T (27 mg, 40 $\mu$mol) followed by HOBT (5 mg, 36 $\mu$mol) and DCC (8 mg, 36 $\mu$mol). The solution was stirred at room temperature for 12 h. The solvent was evaporated, and the residue was purified by column chromatography ($CH_2Cl_2$/MeOH, 5:1, v/v). Resubmitted isolated compound to purification by column chromatography ($CH_2Cl_2$/MeOH, 10:1, v/v) to give 7 mg (17%) of pure compound of formula (15).

Example 2

The monolayer shown in FIG. 1 was designed to release the ligand biotin when a reductive potential is applied to the underlying gold. Monolayers were prepared by immersing gold-coated glass slides in ethanolic solutions containing a mixture of a symmetric disulfide of an alkanethiol substituted with tri(ethylene glycol) and the unsymmetric disulfide of formula (15).

It is preferable that the monolayers remain inert to the non-specific adsorption of protein, both before and after release of the ligand. Accordingly, the monolayers used here present the moiety of the present invention at low density (approximately 1% of total alkanethiolate) surrounded by tri(ethylene glycol) groups because the latter are highly effective at preventing non-specific adsorption of protein (Mrksich, M.; Whitesides, G. M. *American Chemical Society Symposium Series on Chemistry and Biological Applications of Polyethylene Glycol* 1997, 680, 361–373).

Figure 2:
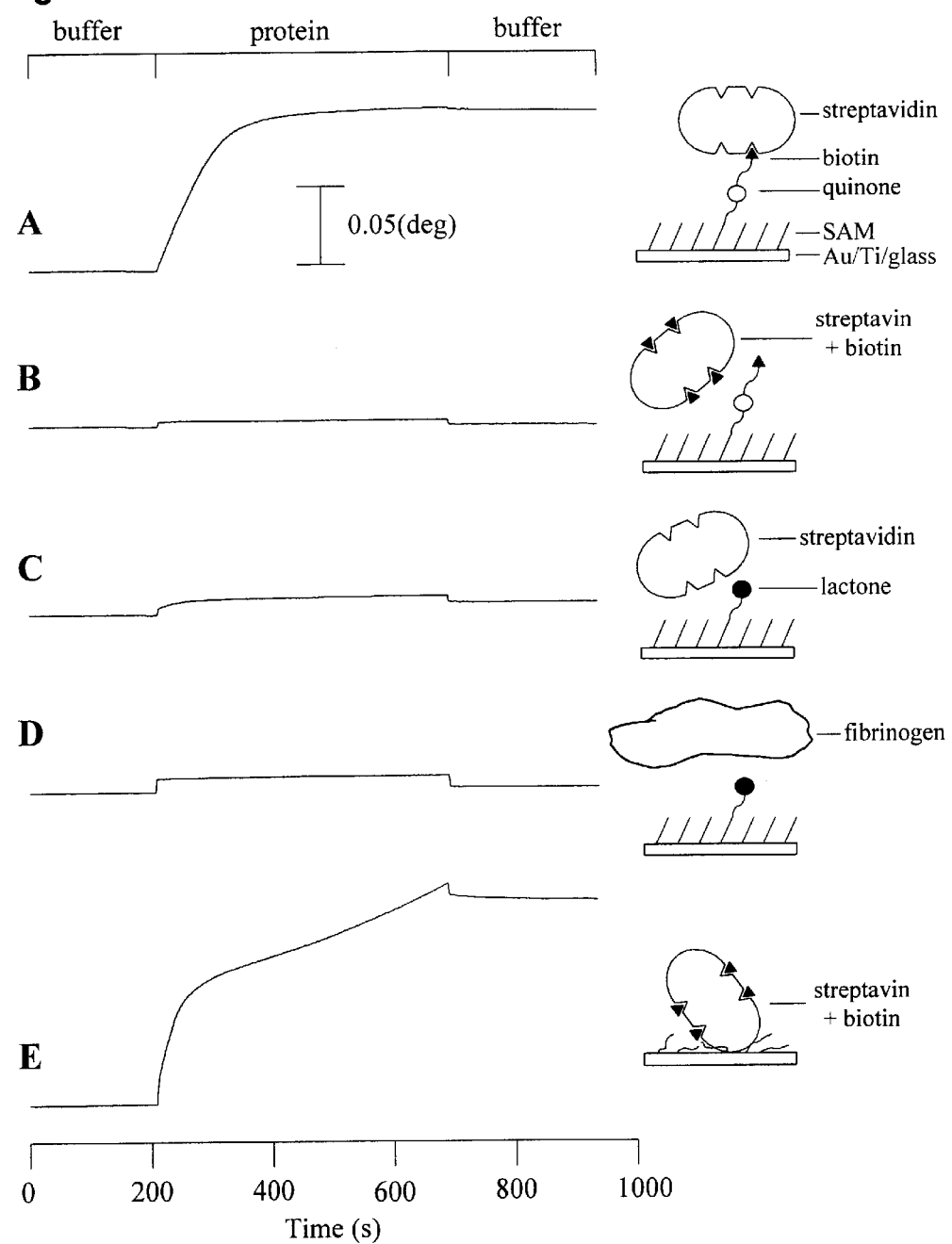
FIG. 2 illustrates SPR data showing the association of proteins with the SAMs; the change in resonance angle ($\Delta\theta$) is plotted on the vertical axis: the scale bar applies to all data, which are offset for clarity.

Surface plasmon resonance (SPR) spectroscopy was used to measure the biospecific association of streptavidin with the monolayer of FIG. 1 and to demonstrate the loss of binding after biotin was electrochemically released (see, for example, Houseman, B. T.; Mrksich, M. *Angew. Chem. Int Ed.* 1999, 38, 782–785; Mrksich, M.; Grunwell, J. R.; Whitesides, G. M. *J. Am. Chem. Soc.* 1995, 117, 12009–12010; and Spinke, J.; Liley, M.; Guder, H. J.; Angermaier, L.; Knoll, W. *Langmuir* 1993, 9, 1821–1825). The following sequence was used to measure the association of proteins to the monolayers: buffer (phosphate buffered saline, pH 7.4) was flowed over the monolayer for three minutes to establish a baseline; a solution of protein in the same buffer was flowed over the surface for eight minutes to observe binding; buffer was again flowed for four minutes to quantitate the amount of protein that remained bound. FIG. 2A shows that streptavidin (60 nM) bound to this monolayer. (SPR measures the angle of light ($\theta$) reflected from the backside of the gold substrate that is a minimum in intensity. Changes in this angle ($\Delta\theta$) are linearly related to the index of refraction of the solution above the surface and therefore to the density of adsorbed protein ($\Delta\theta$ of 0.10°=1 ng/mm$^2$). Experiments show a change in $\theta$ immediately following protein injection due to differences in refractive index between the two solutions.) The change in resonance angle ($\Delta\theta$) after streptavidin was flowed over the substrate corresponds to a final protein density of 1.1 ng/mm$^2$. The protein remained irreversibly bound because of the high affinity of the streptavidin-biotin complex. When the streptavidin was mixed with biotin (140 $\mu$M) before introduction to the SAM, there was no binding of the protein to the surface, demonstrating that the interaction is biospecific (FIG. 2B).

Electrochemistry was performed in buffered water (PBS, pH 7.4) using the gold substrate as the working electrode, a platinum wire as the counter electrode, and a Ag/AgCl/KCl reference electrode—prior to mounting the substrate in a cartridge for analysis by SPR. The reduction and subsequent lactonization and release of biotin were triggered by application of a potential of −700 mV for three minutes. SPR showed that the amount of streptavidin that bound to a SAM treated in this way decreased by 95% (FIG. 2C). The electrochemical treatment did not damage the monolayer or compromise its resistance to non-specific adsorption of several proteins, including the "sticky" protein fibrinogen (0.5 mg/ml) (FIG. 2D). Ellipsometric characterization of the monolayer, at a density of 25% (to increase signal contrast), showed that the thickness decreased by 5 Å after electrochemical treatment, consistent with release of biotin from the surface. Grazing angle FTIR spectra were inconclusive, presumably because of the complexity of the surface.

The use of more extreme potentials (−1100 mV for five minutes) gave monolayers that were no longer inert to non-specific protein adsorption (FIG. 2E), and lower potentials (−600 mV for three minutes) gave incomplete cleavage. As a final control, a monolayer presenting biotin but that did not incorporate the quinone propionic ester tether, was prepared. For this monolayer, application of a potential of −700 mV for three minutes had no effect on the amount of streptavidin that associated, and the monolayer also remained resistant to non-specific protein adsorption. These data establish that ligands tethered to a monolayer, with the present invention, can be selectively released without compromising the inertness of the monolayer.

Example 3

The compound of formula (16) was prepared as outlined in the following synthesis scheme. In the scheme, abbreviations not included in the previous synthetic scheme have the following meanings: DIC is 1,3-diisopropylcarbodiimide; TFA is trifluoroacetic acid; EDT is ethanedithiol; DBU is 1,8-diazabicyclo(5.4.0)undec-7-ene; TBS is t-butyldimethylsilyl; EDC is 1-(3-dimethylaminopropyl)-3-ethylcarbodiimide hydrochloride; and TESH is triethylsilane. The Q/RGD-alkanethiol is the compound of formula (16).

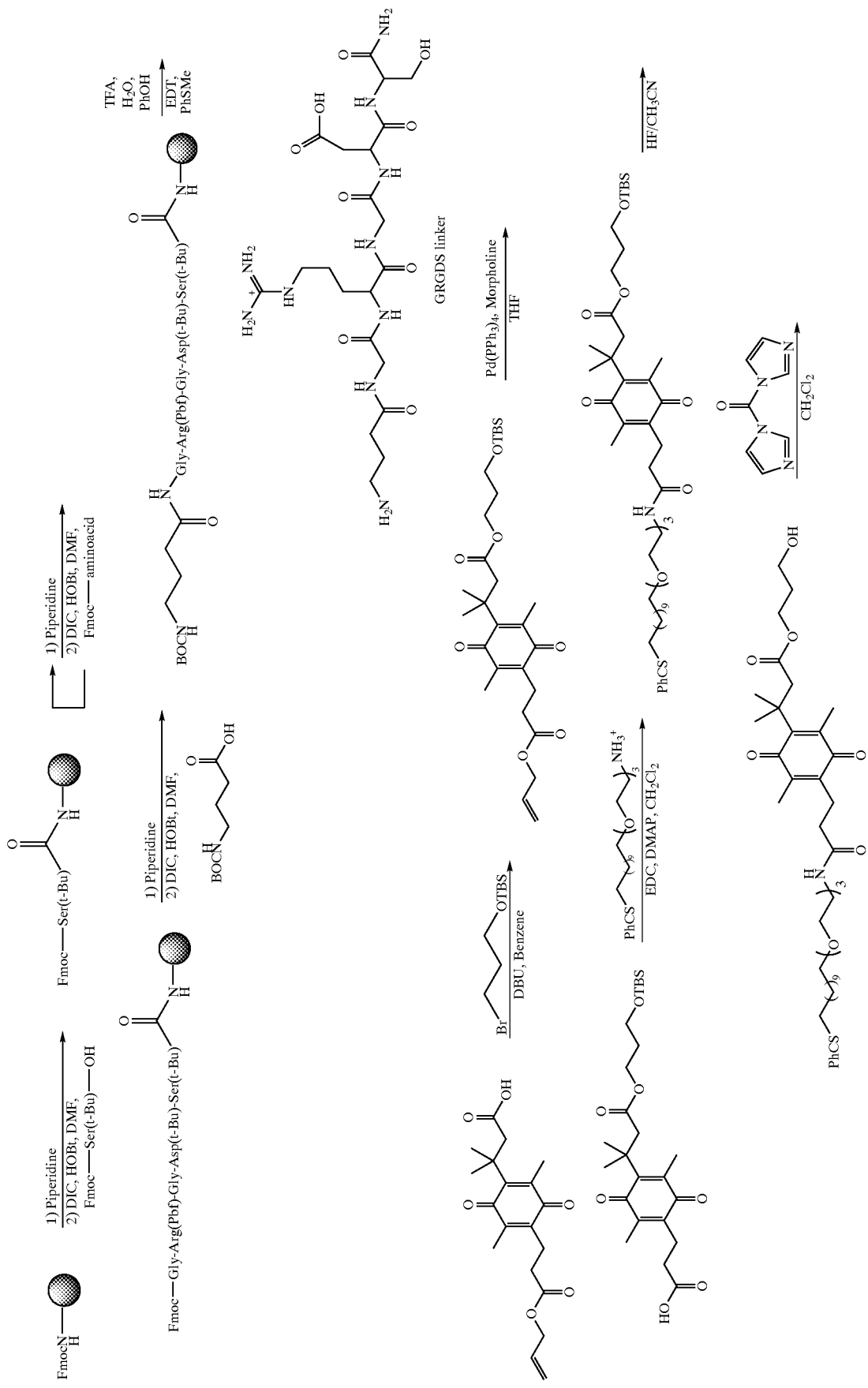

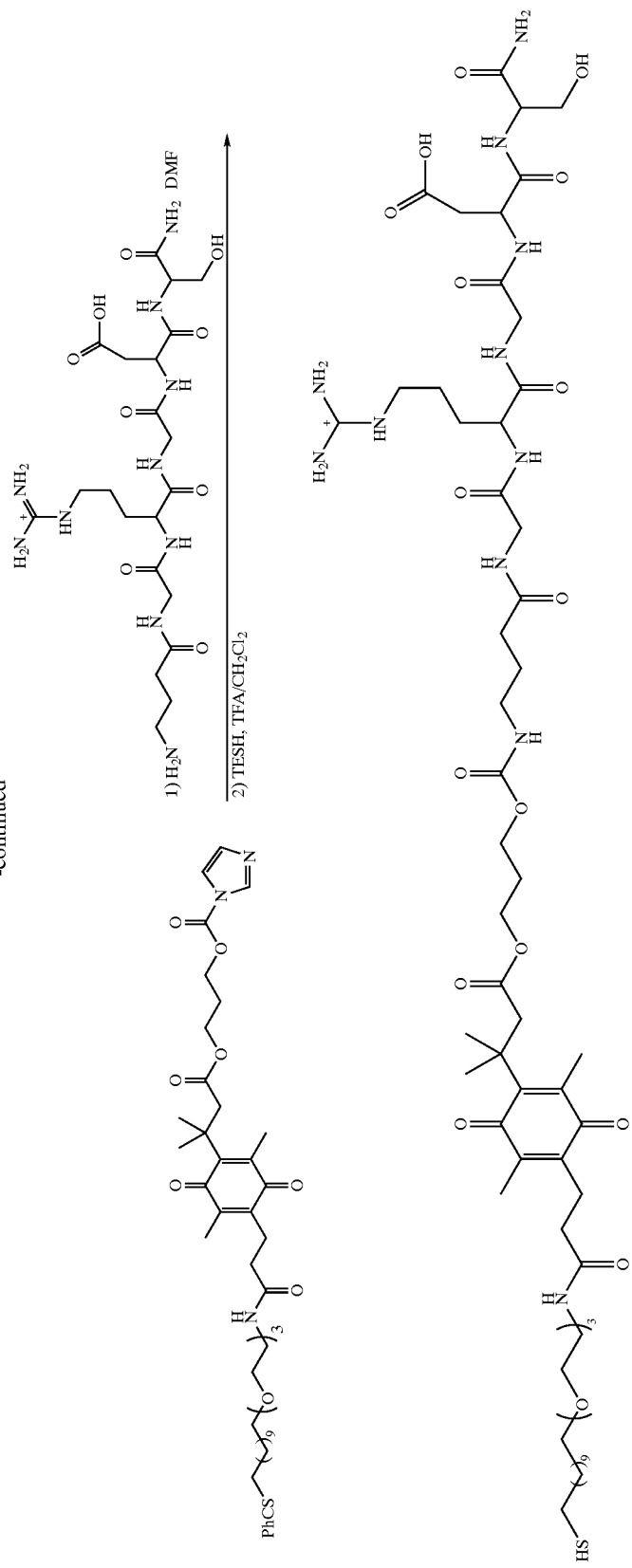

Example 4

Figure 5:
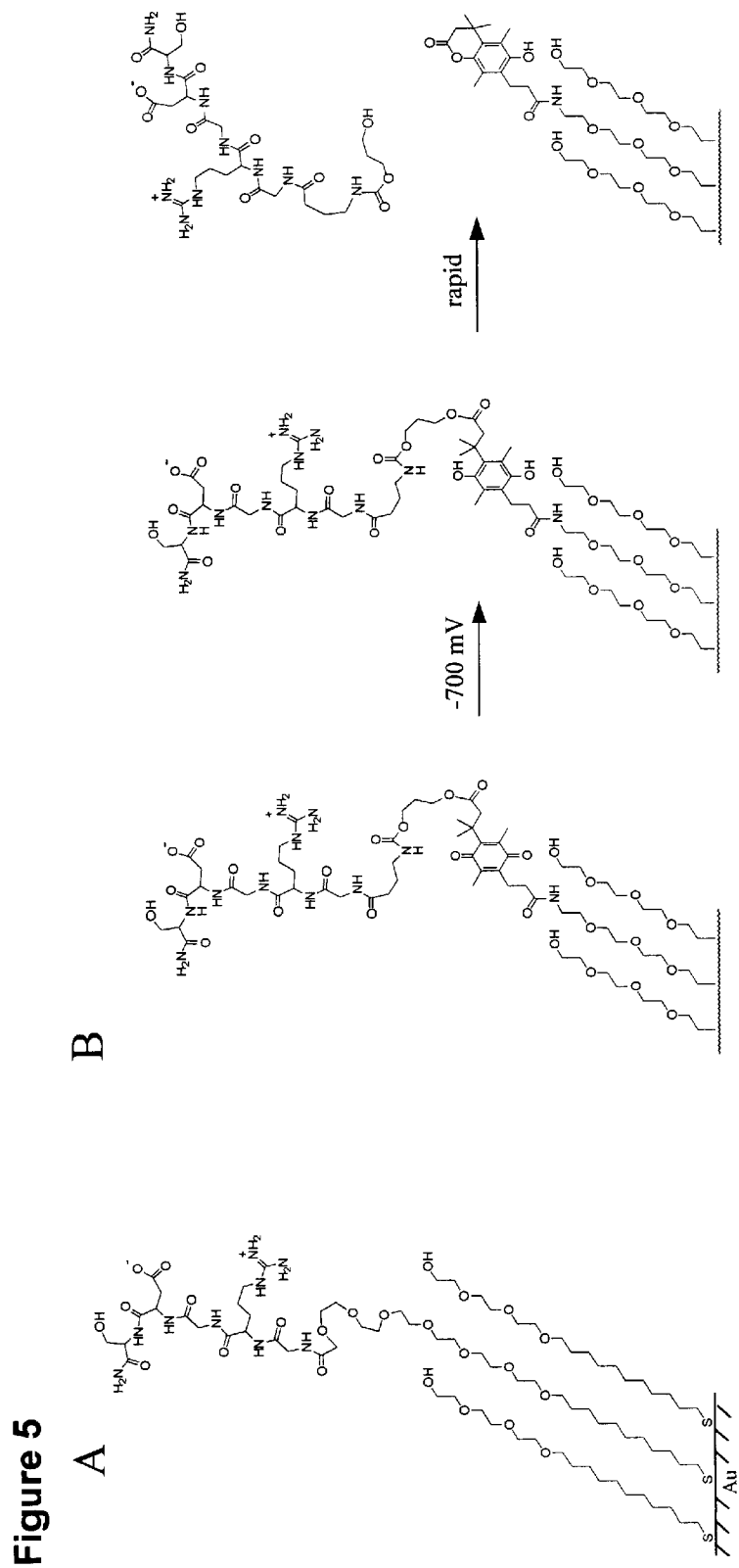
FIGS. 5A and 5B are diagrams of monolayers of alkanethiolates presenting peptide ligands, where the alkanethiolates either contain (5B) or do not contain (5A) an electroactive moiety.

A self-assembled monolayer (SAM) of alkanethiolates of formula (16) on gold, that presents peptide ligands that are tethered to the monolayer, was prepared (FIG. 5B). In this system, the monolayer present, and can release, the tripeptide Arg-Gly-Asp (RGD). This peptide is a ligand found within many extracellular matrix proteins and which mediates cell adhesion via integrin receptors (M. K. Magnusson, D. F. Mosher, *Arterioscler. Thromb. Vasc. Biol.* 1998, 18, 1363–1370; C. Chothia, E. T. Jones, *Annu. Rev. Biochem.* 1997, 66, 823–862; and E. Ruoslahti, *Annu. Rev. Biochem.* 1988, 57, 375–413). In this way, the application of an electrical potential results in the release of RGD, and therefore, of cells that are attached to the monolayer. The tri(ethylene glycol) groups make the substrate inert to non-specific protein adsorption and to non-specific cell adhesion.

The substrate was patterned into two regions that each presented the RGD peptide at a density of less than 0.1% mixed with tri(ethylene glycol) groups. The pattern was formed by applying an alkanethiol solution (corresponding to FIG. 5A) for 5 min to a gold-coated glass substrate, half of which was blocked with a polydimethylsiloxane mask. Following rinsing, the mask was removed, and the substrate was incubated in a solution of a second alkanethiol (corresponding to FIG. 5B) for 6 h. In all cases, the monolayers were formed from ethanolic solutions containing a mixture of an alkanethiol substituted with tri(ethylene glycol) and an alkanethiol substituted with either RGD or the RGD containing alkanethiol of the present invention, in a ratio of 999:1. The two regions differed only in the linkage used to tether the peptides to the monolayer (C. Roberts, C. S. Chen, M. Mrksich, V. Martichonok, D. E. Ingber, G. M. Whitesides, *J. Am. Chem. Soc.* 1998, 120, 6548–6555; and B. T. Houseman, M. Mrksich, *J. Org. Chem.* 1998, 63, 7552–7555). This patterned substrate was used because it simultaneously allows characterization of the selective release of cells, and it shows that the electrical potential does not affect cells on the adjacent region.

Figure 6:
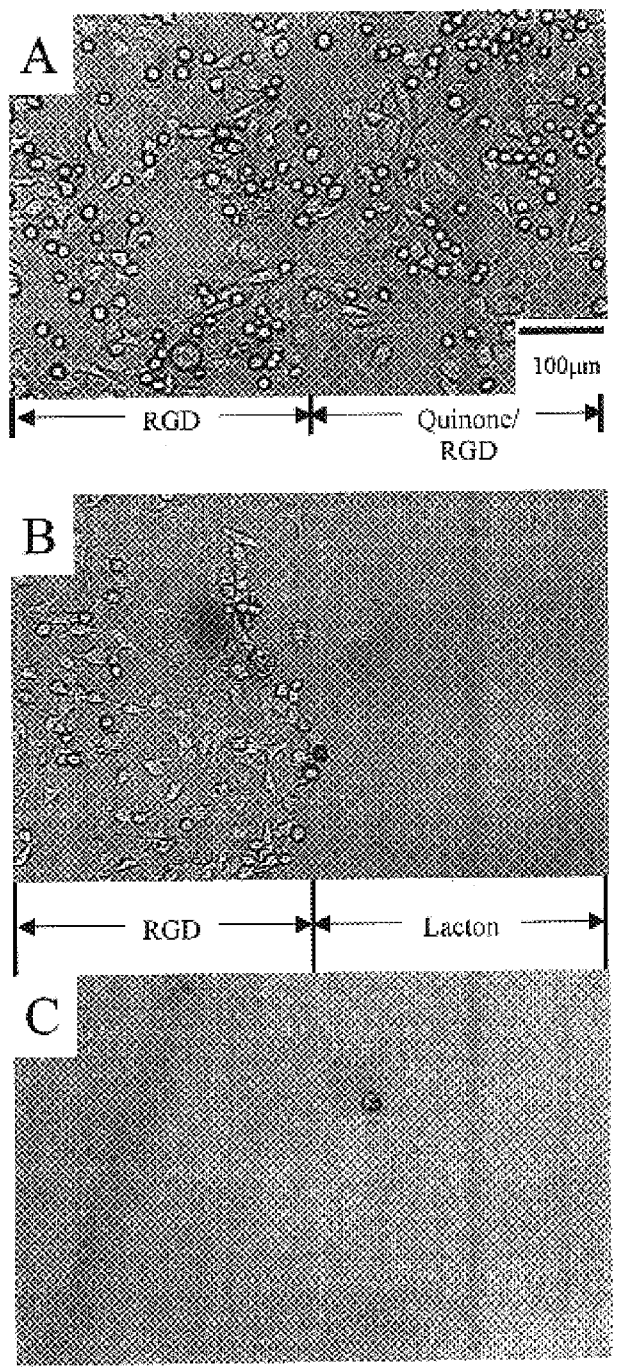
FIGS. 6A through 6C are micrographs of cells on a patterned monolayer, where an electroactive monolayer is present on the right hand side of each micrograph.

This substrate was placed into cell culture media and a suspension of Swiss 3T3 fibroblast cells was added. The Swiss Albino 3T3 cells (ATCC, Rockville, Md.) were grown in Dulbecco's Modified Eagle Medium (DMEM) containing 10% fetal bovine serum and penicillin/streptomycin. All cultures were maintained at 37° C. in a humidified 10% $CO_2$ atmosphere. FIG. 6A shows that cells efficiently attached to both regions of the patterned monolayer. The cells were evenly distributed on the surface and adopted a spread morphology over the entire substrate. After cells were cultured at 37° C. for 30 minutes, an electrical potential of –700 mV (vs. Ag pseudo reference) was applied to the gold substrate for 4 minutes. Electrochemistry was performed in a custom-designed electrochemical cell with the monolayer-coated gold as the working electrode, a Pt wire as the counter electrode, and a Ag wire pseudo reference electrode. All studies were performed using DMEM cell media containing serum at pH 7.4 as solvent and electrolyte.

Immediately after the electrical treatment, more than 70% of the cells on the electroactive regions reverted to a rounded morphology and rested unattached on the substrate. After the substrate was incubated at 37° C. for 10 minutes, the media was replaced with fresh media and the substrate was photographed. FIG. 6B shows that no cells remained on the region of the electroactive monolayer. Cells that were attached to the region of the monolayer presenting the non-releasable RGD, by contrast, were not affected by application of the electrical potential.

As a control experiment, the cell media was replaced with fresh media that contained the soluble peptide Gly-Arg-Gly-Asp-Ser (GRGDS) at a concentration of 2 mM. The substrates were kept at 37° C. for 20 minutes and then removed from the incubator and photographed. FIG. 6C shows that greater than 95% of the cells were released from the surface. This final experiment is important because it shows that the adhesion of cells was mediated only by the RGD peptide, and that the electrical treatment did not compromise the inert property of the substrate; electrical potentials greater than –800 mV can damage the monolayer, making the substrate susceptible to non-specific adhesion, and thereby preventing detachment of cells when soluble peptide is added. A similar inhibition experiment for cells attached to the patterned substrate prior to electrical treatment also resulted in near complete detachment of cells from both regions. To show that the electrical potential did not affect normal cell behavior, a potential of –700 mV was applied for 4 minutes to cells adhered to the surface shown in FIG. 5A. As expected, this short electrical pulse did not affect cell morphology, and cells continued to grow and divide normally. These results show that cell adhesion to the monolayers is biospecific and that the RGD ligand can be released from the substrate selectively, without consequence to cells attached to other ligands.

Obviously, numerous modifications and variations of the present invention are possible in light of the above teachings. It is therefore to be understood that within the scope of the appended claims, the invention may be practiced otherwise than as specifically described herein.

What is claimed is:

1. An alkanethiol of formula (1):

HS—L—Q$^1$—T—Q$^2$—M—G—Z   (1), wherein —L— is 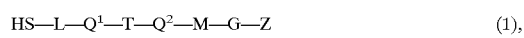;

each $A^L$, $B^L$, $E^L$ and $D^L$ are individually $C(R^L_A R^L_A{}')$—, —C($R^L_B R^L_B{}'$)—, —C($R^L_E R^L_E{}'$)—, and —C($R^L_D R^L_D{}'$)—, respectively;

each $R^L_A$, $R^L_B$, $R^L_E$ and $R^L_D$ are individually H, or any two of $R^L_A$, $R^L_B$, $R^L_E$ and $R^L_D$ together form a bond, or $R^L_A$, $R^L_B$, $R^L_E$ and $R^L_D$ together with the atoms to which they are bonded form a six-membered aromatic ring;

each $R^L_A{}'$, $R^L_B{}'$, $R^L_E{}'$ and $R^L_D{}'$ are individually H, or any two of $R^L_A{}'$, $R^L_B{}'$, $R^L_E{}'$ and $R^L_D{}'$ together form a bond, or $R^L_A{}'$, $R^L_B{}'$, $R^L_E{}'$ and $R^L_D{}'$ together with the atoms to which they are bonded form a six-membered aromatic ring;

each j, k and l are individually either 0 or 1;

m is 1 to 5;

—Q$^1$— and —Q$^2$— are each individually selected from the group consisting of

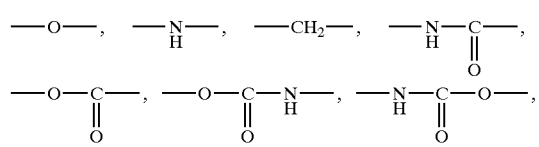

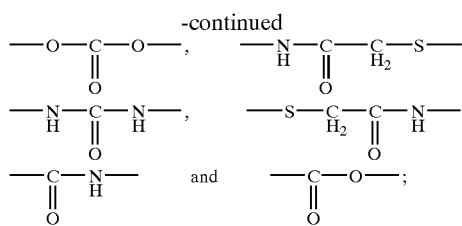

—T— is a moiety of formula (2) or formula (3)

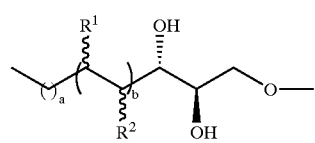

—(OCH$_2$CH$_2$)$_n$O— (3)

$R^1$ and $R^2$ are each individually selected from the group consisting of H and OH;

a is 0 to 3;

b is 0 to 3;

∼∼∼ indicates that the chirality of the carbon atom to which it is attached may be either R or S;

n is 1 to 6;

—M— is —(A$_x$—B$_y$—E$_z$—D)$_w$—;

A is —O—, —S—, —N(R$_A$)— or —C(R$_A$R$_A$')—;

B is —O—, —S—, —N(R$_B$)— or —C(R$_B$R$_B$')—;

E is —O—, —S—, —N(R$_E$)— or —C(R$_E$R$_E$')—;

D is —C(R$_D$R$_D$')—;

each R$_A$, R$_B$, R$_E$ and R$_D$ is selected from the group consisting of H, alkyl, alkenyl, alkynyl, aryl and heterocyclic radical, or any two of R$_A$, R$_B$, R$_E$ and R$_D$ together form a bond, or any two of R$_A$, R$_B$, R$_E$ and R$_D$ together with the atoms to which they are bonded for a ring;

each R$_A$', R$_B$', R$_E$' and R$_D$' is selected from the group consisting of H, alkyl, alkenyl, alkynyl, aryl and heterocyclic radical, or any two of R$_A$', R$_B$', R$_E$' and R$_D$' together form a bond, or any two of R$_A$', R$_B$', R$_E$' and R$_D$' together with the atoms to which they are bonded for a ring;

each x, y and z is either 0 or 1;

—G— is a moiety of formula (4)

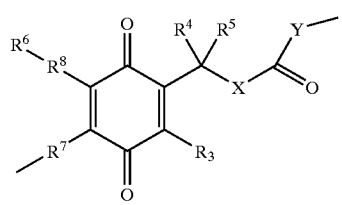

$R^3$, $R^4$, and $R^5$ are each individually a —CH$_2$— group substituted with a hydrogen or an alkyl group;

$R^6$ is a hydrogen, alkyl, alkenyl, alkynyl, aryl, halogen, heterocyclic radical or nitro group;

X is a bond or —(A$^x_p$—B$^x_q$—E$^x_r$—D$^x$)$_s$—;

each A$^x$, B$^x$, E$^x$ and D$^x$ is individually C(R$^x_A$R$^x_A$')—, —C(R$^x_B$R$^x_B$')—, —C(R$^x_E$R$^x_E$')—, or —C(R$^x_D$R$^x_D$')—, respectively;

each R$^x_A$, R$^x_B$, R$^x_E$ and R$^x_D$ is individually H, or any two of R$^x_A$, R$^x_B$, R$^x_E$ and R$^x_D$ together form a bond, or R$^x_A$, R$^x_B$, R$^x_E$ and R$^x_D$ together with the atoms to which they are bonded form a six-membered aromatic ring;

each R$^x_A$', R$^x_B$', R$^x_E$' and R$^x_D$' is individually H, or any two of R$^x_A$', R$^x_B$', R$^x_E$' and R$^x_D$' together form a bond, or R$^x_A$', R$^x_B$', R$^x_E$' and R$^x_D$' together with the atoms to which they are bonded form a six-membered aromatic ring;

each p, q and r is individually either 0 or 1;

s is 1 to 5;

Y is —O— or —NH—;

R$^7$ and R$^8$ are both single bonds, or together with the atoms to which they are bonded from one or more fused rings, substituted or unsubstituted, optionally containing heteroatoms; and —Z is a leaving group.

2. The alkanethiol of claim 1, wherein —T— is a moiety of formula (3)

—(OCH$_2$CH$_2$)$_n$O— (3).

3. The alkanethiol of claim 1, wherein —Q$^2$— is selected from the group consisting of

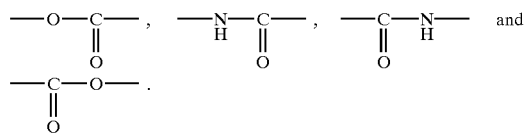

4. The alkanethiol of claim 1, wherein —L— contains 8 to 18 carbon atoms.

5. The alkanethiol of claim 1, wherein —M— is an alkylene group containing 1 to 10 carbon atoms.

6. The alkanethiol of claim 1, wherein —G— is a moiety of formula (4')

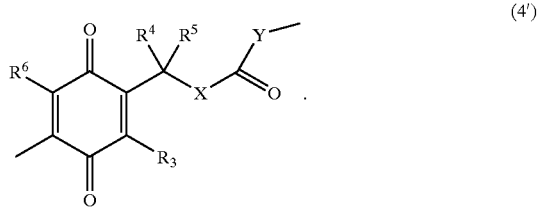

7. The alkanethiol of claim 1, wherein —Q$^1$— is —O— or —CH$_2$—.

8. The alkanethiol of claim 6, wherein —L— is an alkylene containing 6 to 18 carbon atoms, and —Q$^1$— is —O—.

9. A disulfide of formula (5):

J—S—S—L—Q$^1$—T—Q$^2$—M—G—Z           (5), wherein —L— is $-(A^L_j-B^L_k-E^L_l-D^L)_m-$;

each $A^L$, $B^L$, $E^L$ and $D^L$ are individually $C(R^L_A R^L_A{}')-$, $-C(R^L_B R^L_B{}')-$, $-C(R^L_E R^L_E{}')-$, and $-C(R^L_D R^L_D{}')-$, respectively;

each $R^L_A$, $R^L_B$, $R^L_E$ and $R^L_D$ are individually H, or any two of $R^L_A$, $R^L_B$, $R^L_E$ and $R^L_D$ together form a bond, or $R^L_A$, $R^L_B$, $R^L_E$ and $R^L_D$ together with the atoms to which they are bonded form a six-membered aromatic ring;

each $R^L_A{}'$, $R^L_B{}'$, $R^L_E{}'$ and $R^L_D{}'$ are individually H, or any two of $R^L_A{}'$, $R^L_B{}'$, $R^L_E{}'$ and $R^L_D{}'$ together form a bond, or $R^L_A{}'$, $R^L_B{}'$, $R^L_E{}'$ and $R^L_D{}'$ together with the atoms to which they are bonded form a six-membered aromatic ring;

each j, k and l are individually either 0 or 1;

m is 1 to 5;

—Q$^1$— and —Q$^2$— are each individually selected from the group consisting of

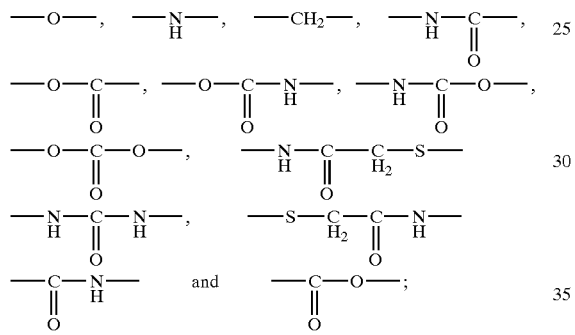

—T— is a moiety of formula (2) or formula (3)

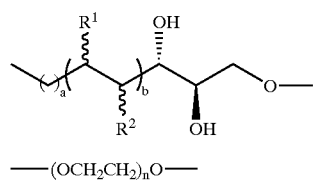

(2)

(3)

$R^1$ and $R^2$ are each individually selected from the group consisting of H and OH;

a is 0 to 3;

b is 0 to 3;

∼∼∼ indicates that the chirality of the carbon atom to which it is attached may be either R or S;

n is 1 to 6;

—M— is $-(A_x-B_y-E_z-D)_w-$;

A is —O—, —S—, —N($R_A$)— or —C($R_A R_A{}'$)—;

B is —O—, —S—, —N($R_B$)— or —C($R_B R_B{}'$)—;

E is —O—, —S—, —N($R_E$)— or —C($R_E R_E{}'$)—;

D is —C($R_D R_D{}'$)—;

each $R_A$, $R_B$, $R_E$ and $R_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded for a ring;

each $R_A{}'$, $R_B{}'$, $R_E{}'$ and $R_D{}'$ is selected from the group consisting of H, alkyl, alkenyl, alkynyl, aryl and heterocyclic radical, or any two of $R_A{}'$, $R_B{}'$, $R_E{}'$ and $R_D{}'$ together form a bond, or any two $R_A{}'$, $R_B{}'$, $R_E{}'$ and $R_D{}'$ together with the atoms to which they are bonded for a ring;

each x, y and z is either 0 or 1;

—G— is a moiety of formula (4)

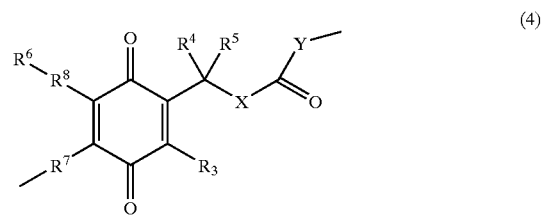

(4)

$R^3$, $R^4$, and $R^5$ are each individually a —CH$_2$— group substituted with a hydrogen or an alkyl group;

$R^6$ is a hydrogen, alkyl, alkenyl, alkynyl, aryl, halogen, heterocyclic radical or nitro group;

X is a bond or $-(A^x_p B^x_q E^x_r-D^x)_s-$;

each $A^x$, $B^x$, $E^x$ and $D^x$ is individually $C(R^x_A R^x_A{}')-$, $-C(R^x_B R^x_B{}')-$, $-C(R^x_E R^x_E{}')-$, or $-C(R^x_D R^x_D{}')-$, respectively;

each $R^x_A$, $R^x_B$, $R^x_E$ and $R^x_D$ is individually H, or any two of $R^x_A$, $R^x_B$, $R^x_E$ and $R^x_D$ together form a bond, or $R^x_A$, $R^x_B$, $R^x_E$ and $R^x_D$ together with the atoms to which they are bonded form a six-membered aromatic ring;

each $R^x_A{}'$, $R^x_B{}'$, $R^x_E{}'$ and $R^x_D{}'$ is individually H, or any two of $R^x_A{}'$, $R^x_B{}'$, $R^x_E{}'$ and $R^x_D{}'$ together form a bond, or $R^x_A{}'$, $R^x_B{}'$, $R^x_E{}'$ and $R^x_D{}'$ together with the atoms to which they are bonded form a six-membered aromatic ring;

each p, q and r is individually either 0 or 1;

s is 1 to 5;

Y is —O— or —NH—;

$R^7$ and $R^8$ are both single bonds, or together with the atoms to which they are bonded from one or more fused rings, substituted or unsubstituted, optionally containing heteroatoms;

—Z is a leaving group

—J is selected from the group consisting of H, halogen, R, —OR, —NRR', —C(O)R, and —C(O)OR;

R is selected from the group consisting of alkyl, alkenyl, alkynyl, aryl and heterocyclic radical; and R' is selected from the group consisting of H, alkyl, alkenyl, alkynyl, aryl and heterocyclic radical.

10. The disulfide of claim 9, wherein —J is a moiety of formula (6)

wherein t is 2 to 20, and u is 2 to 10.

11. The disulfide of claim 9, wherein —T— is a moiety of formula (3)

12. The disulfide of claim 9, wherein —Q²— is selected from the group consisting of

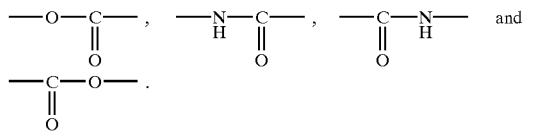

13. The disulfide of claim 9, wherein —L— contains 8 to 18 carbon atoms.

14. The disulfide of claim 9, wherein —M— is an alkylene group containing 1 to 10 carbon atoms.

15. The disulfide of claim 9, wherein —G— is a moiety of formula (4')

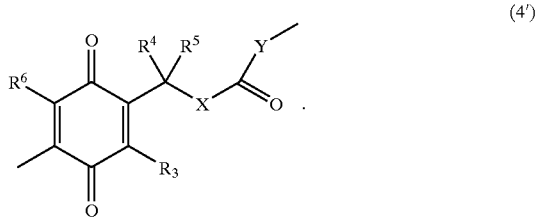

16. The disulfide of claim 9, wherein —Q¹— is —O— or —CH₂—.

17. The disulfide of claim 15, wherein —L— is an alkylene containing 6 to 18 carbon atoms, and —Q¹— is —O—.

18. A substrate, comprising:
(i) a surface layer comprising gold, and
(ii) a plurality of moieties, on at least a portion of said surface layer, wherein said moieties are alkanethiolate moieties of formula (8):

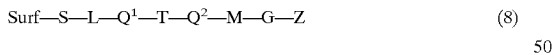

wherein —L— is —(A$^L_j$—B$^L_K$—E$^L_l$—D$^L$)$_m$—;

each A$^L$, B$^L$, E$^L$ and D$^L$ are individually C(R$^L_A$R$^L_A$')—, —C(R$^L_B$R$^L_B$')—, —C(R$^L_E$R$^L_E$')—, and —C(R$^L_D$R$^L_D$')—, respectively;

each R$^L_A$, R$^L_B$, R$^L_E$ and R$^L_D$ are individually H, or any two of R$^L_A$, R$^L_B$, R$^L_E$ and R$^L_D$ together form a bond, or R$^L_A$, R$^L_B$, R$^L_E$ and R$^L_D$ together with the atoms to which they are bonded form a six-membered aromatic ring;

each R$^L_A$', R$^L_B$', R$^L_E$' and R$^L_D$' are individually H, or any two of R$^L_A$', R$^L_B$', R$^L_E$' and R$^L_D$' together form a bond, or R$^L_A$', R$^L_B$', R$^L_E$' and R$^L_D$' together with the atoms to which they are bonded form a six-membered aromatic ring;

each j, k and l are individually either 0 or 1;

m is 1 to 5;

—Q¹— and —Q²— are each individually selected from the group consisting of

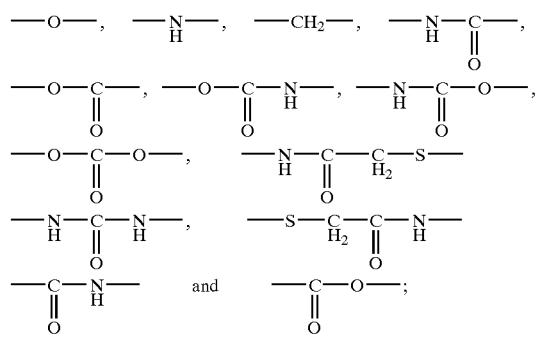

—T— is a moiety of formula (2) formula (3)

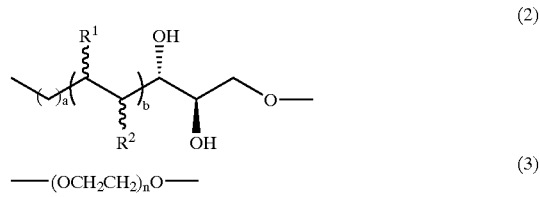

R¹ and R² are each individually selected from the group consisting of H and OH;

a is 0 to 3;

b is 0 to 3;

∼∼∼ indicates that the chirality of the carbon atom to which it is attached may be either R or S;

n is 1 to 6;

—M— is —(A$_x$—B$_y$—E$_z$—D)$_w$—;

A is —O—, —S—, —N(R$_A$)— or —C(R$_A$R$_A$')—;

B is —O—, —S—, —N(R$_B$)— or —C(R$_B$R$_B$')—;

E is —O—, —S—, —N(R$_E$)— or —C(R$_E$R$_E$')—;

D is —C(R$_D$R$_D$')—;

each R$_A$, R$_B$, R$_E$ and R$_D$ is selected from the group consisting of H, alkyl, alkenyl, alkynyl, aryl and heterocyclic radical, or any two of R$_A$, R$_B$, R$_E$ and R$_D$ together form a bond, or any two of R$_A$, R$_B$, R$_E$ and R$_D$ together with the atoms to which they are bonded for a ring;

each R$_A$', R$_B$', R$_E$' and R$_D$' is selected from the group consisting of H, alkyl, alkenyl, alkynyl, aryl and heterocyclic radical, or any two of R$_A$', R$_B$', R$_E$' and R$_D$' together form a bond, or any two of R$_A$', R$_B$', R$_E$' and R$_D$' together with the atoms to which they are bonded for a ring;

each x, y and z is either 0 or 1;

—G— is a moiety of formula (4)

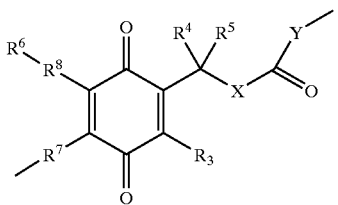

(4)

$R^3$, $R^4$, and $R^5$ are each individually a —CH$_2$— group substituted with a hydrogen or an alkyl group;

$R^6$ is a hydrogen, alkyl, alkenyl, alkynyl, aryl, halogen, heterocyclic radical or nitro group;

X is a bond or —(A$^x_p$—B$^x_q$—E$^x_r$—D$^x$)$_s$—;

each A$^x$, B$^x$, E$^x$ and D$^x$ is individually C(R$^x_A$R$^x_A{}'$)—, —C(R$^x_B$R$^x_B{}'$)—, —C(R$^x_E$R$^x_E{}'$)—, or —C(R$^x_D$R$^x_D{}'$)—, respectively;

each R$^x_A$, R$^x_B$, R$^x_E$ and R$^x_D$ is individually H, or any two of R$^x_A$, R$^x_B$, R$^x_E$ and R$^x_D$ together form a bond, or R$^x_A$, R$^x_B$, R$^x_E$ and R$^x_D$ together with the atoms to which they are bonded form a six-membered aromatic ring;

each R$^x_A{}'$, R$^x_B{}'$, R$^x_E{}'$ and R$^x_D{}'$ is individually H, or any two of R$^x_A{}'$, R$^x_B{}'$, R$^x_E{}'$ and R$^x_D{}'$ together form a bond, or R$^x_A{}'$, R$^x_B{}'$, R$^x_E{}'$ and R$^x_D{}'$ together with the atoms to which they are bonded form a six-membered aromatic ring;

each p, q and r is individually either 0 or 1;

s is 1 to 5;

Y is —O— or —NH—;

$R^7$ and $R_8$ are both single bonds, or together with the atoms to which they are bonded from one or more fused rings, substituted or unsubstituted, optionally containing heteroatoms;

—Z is a leaving group; and

Surf designates where the moiety attaches to said surface.

19. The substrate of claim 18, further comprising:
(iii) a patterned monolayer comprising said moieties.

20. The substrate of claim 18, further comprising:
(iv) a base,
wherein said surface layer is on said base.

21. The substrate of claim 18, wherein —T— is a moiety of formula (3)

—(OCH$_2$CH$_2$)$_n$O— (3).

22. The substrate of claim 18, wherein —Q$^2$— is selected from the group consisting of

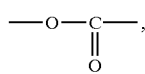, 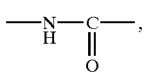,

-continued
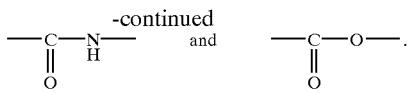

23. The substrate of claim 18, wherein —L— contains 8 to 18 carbon atoms.

24. The substrate of claim 18, wherein —M— is an alkylene group containing 1 to 10 carbon atoms.

25. The substrate of claim 18, wherein —G— is a moiety of formula (4')

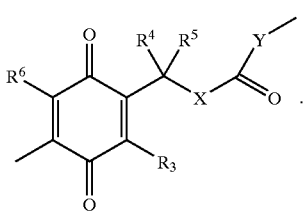

(4')

26. The substrate of claim 18, wherein —Q$^1$— is —O— or —CH$_2$—.

27. The substrate of claim 25, wherein —L— is an alkylene containing 6 to 18 carbon atoms, and —Q$^1$— is —O—.

28. A cell chip, comprising:
(A) the substrate of claim 18, and
(B) cells, on said substrate.

29. A protein chip, comprising:
(A) the substrate of claim 18,
wherein —Z comprises protein.

30. A method of making a substrate, comprising contacting a surface with the alkanethiol of claim 1;
wherein said surface comprises gold.

31. A method of making a substrate, comprising contacting a surface with the alkanethiol of claim 2;
wherein said surface comprises gold.

32. A method of making a substrate, comprising contacting a surface with the alkanethiol of claim 8;
wherein said surface comprises gold.

33. A method of making a substrate, comprising contacting a surface with the disulfide of claim 9;
wherein said surface comprises gold.

34. A method of making a substrate, comprising contacting a surface with the disulfide of claim 11;
wherein said surface comprises gold.

35. A method of making a substrate, comprising contacting a surface with the disulfide of claim 12;
wherein said surface comprises gold.

36. A method of making a substrate, comprising contacting a surface with the disulfide of claim 17;
wherein said surface comprises gold.

37. A method of making a cell chip, comprising:
contacting cells with the substrate of claim 18.

38. The method of claim 37, further comprising allowing said cells to proliferate.

39. A method of making a protein chip, comprising:
contacting protein with the substrate of claim 20.

40. A method of releasing a leaving group, comprising:
applying a reducing potential to a surface comprising a self assembled monolayer comprising alkanethiolates terminated with the leaving group.

41. A method of releasing a leaving group, comprising:
applying a reducing potential to a surface;
wherein said leaving group is attached to said surface through a moiety —G— of formula (4)

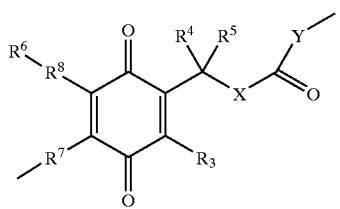

(4)

wherein $R^3$, $R^4$, and $R^5$ are each individually a —CH$_2$— group substituted with a hydrogen or an alkyl group;

$R^6$ is a hydrogen, alkyl, alkenyl, alkynyl, aryl, halogen, heterocyclic radical or nitro group;

X is a bond or —$(A^X_p$—$B^X_q$—$E^X_r$—$D^X)_s$—;

each $A^X$, $B^X$, $E^X$ and $D^X$ is individually $C(R^X_A R^X_A{}')$—, —$C(R^X_B R^X_B{}')$—, —$C(R^X_E R^X_E{}')$—, or —$C(R^X_D R^X_D{}')$—, respectively;

each $R^X_A$, $R^X_B$, $R^X_E$ and $R^X_D$ is individually H, or any two of $R^X_A$, $R^X_B$, $R^X_E$ and $R^X_D$ together form a bond, or $R^X_A$, $R^X_B$, $R^X_E$ and $R^X_D$ together with the atoms to which they are bonded form a six-membered aromatic ring;

each $R^X_A{}'$, $R^X_B{}'$, $R^X_E{}'$ and $R^X_D{}'$ is individually H, or any two of $R^X_A{}'$, $R^X_B{}'$, $R^X_E{}'$ and $R^X_D{}'$ together form a bond, or $R^X_A{}'$, $R^X_B{}'$, $R^X_E{}'$ and $R^X_D{}'$ together with the atoms to which they are bonded form a six-membered aromatic ring;

each p, q and r is individually either 0 or 1;

s is 1 to 5;

Y is —O— or —NH—;

$R^7$ and $R_B$ are both single bonds, or together with the atoms to which they are bonded from one or more fused rings, substituted or unsubstituted, optionally containing heteroatoms.

42. The method of claim 41, wherein —G— is a moiety of formula (4')

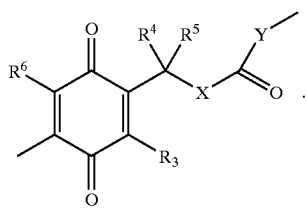

(4')

43. The method of claim 40, wherein the reducing potential has a magnitude ranging from −700 mV to −2 V.

44. The method of claim 40, wherein the alkanethiolates are of formula (1):

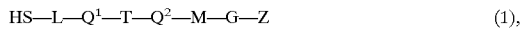

HS—L—$Q^1$—T—$Q^2$—M—G—Z    (1), wherein —L— is —$(A^L_j$—$B^L_k$—$E^L_l$—$D^L)_m$—;

each $A^L$, $B^L$, $E^L$ and $D^L$ are individually $C(R^L_A R^L_A{}')$—, —$C(R^L_B R^L_B{}')$—, —$C(R^L_E R^L_E{}')$—, and —$C(R^L_D R^L_D{}')$—, respectively;

each $R^L_A$, $R^L_B$, $R^L_E$ and $R^L_D$ are individually H, or any two of $R^L_A$, $R^L_B$, $R^L_E$ and $R^L_D$ together form a bond, or $R^L_A$, $R^L_B$, $R^L_E$ and $R^L_D$ together with the atoms to which they are bonded form a six-membered aromatic ring;

each $R^L_A{}'$, $R^L_B{}'$, $R^L_E{}'$ and $R^L_D{}'$ are individually H, or any two of $R^L_A{}'$, $R^L_B{}'$, $R^L_E{}'$ and $R^L_D{}'$ together form a bond, or $R^L_A{}'$, $R^L_B{}'$, $R^L_E{}'$ and $R^L_D{}'$ together with the atoms to which they are bonded form a six-membered aromatic ring;

each j, k and l are individually either 0 or 1;

m is 1 to 5;

—$Q^1$— and —$Q^2$— are each individually selected from the group consisting of

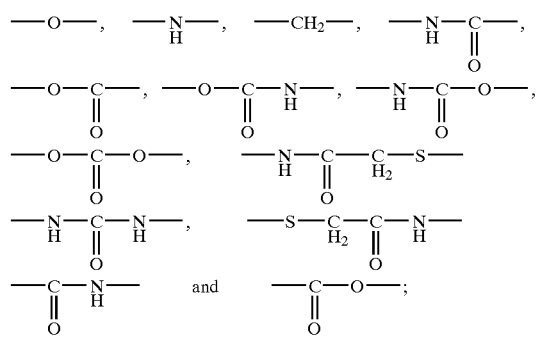

—T— is a moiety of formula (2) or formula (3)

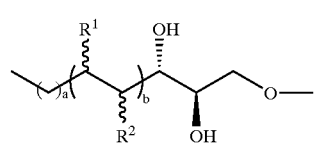

(2)

—(OCH$_2$CH$_2$)$_n$O—    (3)

$R^1$ and $R^2$ are each individually selected from the group consisting of H and OH;

a is 0 to 3;

b is 0 to 3;

∿∿∿ indicates that the chirality of the carbon atom to which it is attached may be either R or S;

n is 1 to 6;

—M— is —$(A_x$—$B_y$—$E_z$—$D)_w$—;

A is —O—, —S—, —N($R_A$)— or —C($R_A R_A{}'$)—;

B is —O—, —S—, —N($R_B$)— or —C($R_B R_B'$)—;

E is —O—, —S—, —N($R_E$)— or —C($R_E R_E'$)—;

D is —C($R_D R_D'$)—;

each $R_A$, $R_B$, $R_E$ and $R_D$ is selected from the group consisting of H, alkyl, alkenyl, alkynyl, aryl and heterocyclic radical, or any two of $R_A$, $R_B$, $R_E$ and $R_D$ together form a bond, or any two of $R_A$, $R_B$, $R_E$ and $R_D$ together with the atoms to which they are bonded for a ring;

each $R_A'$, $R_B'$, $R_E'$ and $R_D'$ is selected from the group consisting of H, alkyl, alkenyl, alkynyl, aryl and heterocyclic radical, or any two of $R_A'$, $R_B'$, $R_E'$ and $R_D'$ together form a bond, or any two $R_A'$, $R_B'$, $R_E'$ and $R_D'$ together with the atoms to which they are bonded for a ring;

each x, y and z is either 0 or 1;

—G— is a moiety of formula (4); and

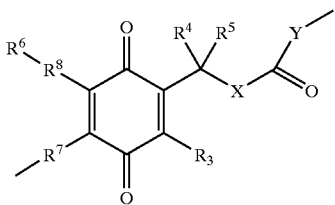

(4)

—Z is a leaving group.

45. The method of claim 40, wherein the alkanethiolates are patterned on at least a portion of the surface.

46. The method of claim 45, wherein the surface is gold.

47. The method of claim 40, wherein the leaving group comprises a protein.

48. The method of claim 40, wherein the leaving group comprises a carbohydrate.

49. The method of claim 40, wherein the leaving group comprises a diene or dienophile.

50. The method of claim 41, wherein the surface is gold.

* * * * *